US012502173B2

(12) United States Patent
Fernandes et al.

(10) Patent No.: US 12,502,173 B2
(45) Date of Patent: Dec. 23, 2025

(54) SURGICAL STAPLING DEVICE WITH JAWS THAT PIVOT BETWEEN AN OPEN POSITION AND A CLAMPED POSITION

(71) Applicant: Covidien LP, Mansfield, MA (US)

(72) Inventors: Roanit A. Fernandes, Hamden, CT (US); Matthew J. Chowaniec, Madison, CT (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 18/653,347

(22) Filed: May 2, 2024

(65) Prior Publication Data

US 2024/0374256 A1 Nov. 14, 2024

Related U.S. Application Data

(60) Provisional application No. 63/464,992, filed on May 9, 2023.

(51) Int. Cl.
*A61B 17/072* (2006.01)
*A61B 17/29* (2006.01)

(52) U.S. Cl.
CPC .................. *A61B 17/07207* (2013.01); *A61B 2017/07271* (2013.01); *A61B 2017/2929* (2013.01)

(58) Field of Classification Search
CPC .... A61B 17/07207; A61B 2017/07271; A61B 2017/2929
See application file for complete search history.

(56) References Cited

U.S. PATENT DOCUMENTS

| | | | |
|---|---|---|---|
| 3,499,591 | A | 3/1970 | Green |
| 3,777,538 | A | 12/1973 | Weatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |
| 4,589,413 | A | 5/1986 | Malyshev et al. |
| 4,596,351 | A | 6/1986 | Fedotov et al. |
| 4,602,634 | A | 7/1986 | Barkley |
| 4,605,001 | A | 8/1986 | Rothfuss et al. |
| 4,608,981 | A | 9/1986 | Rothfuss et al. |

(Continued)

FOREIGN PATENT DOCUMENTS

| | | |
|---|---|---|
| AU | 198654765 | 9/1986 |
| CA | 2773414 A1 | 11/2012 |

(Continued)

*Primary Examiner* — Michelle Lopez

(57) ABSTRACT

A surgical stapling device includes a drive assembly and a tool assembly having an anvil and a cartridge assembly that is pivotably coupled to the anvil for movement between an open position and a clamped position. The cartridge assembly includes a staple cartridge and a channel member that defines a cavity that receives the staple cartridge. The channel member includes a channel lock that is positioned on a proximal portion of the channel member. The drive assembly is movable between a drive advanced position and a drive retracted position and engages the channel lock in the drive retracted position to retain the tool assembly in the open position.

18 Claims, 7 Drawing Sheets

(56) References Cited

U.S. PATENT DOCUMENTS

| | | | |
|---|---|---|---|
| 4,610,383 | A | 9/1986 | Rothfuss et al. |
| 4,633,861 | A | 1/1987 | Chow et al. |
| 4,633,874 | A | 1/1987 | Chow et al. |
| 4,671,445 | A | 6/1987 | Barker et al. |
| 4,700,703 | A | 10/1987 | Resnick et al. |
| 4,703,887 | A | 11/1987 | Clanton et al. |
| 4,728,020 | A | 3/1988 | Green et al. |
| 4,752,024 | A | 6/1988 | Green et al. |
| 4,784,137 | A | 11/1988 | Kulik et al. |
| 4,863,088 | A | 9/1989 | Redmond et al. |
| 4,869,415 | A | 9/1989 | Fox |
| 4,892,244 | A | 1/1990 | Fox et al. |
| 4,955,959 | A | 9/1990 | Tompkins et al. |
| 4,978,049 | A | 12/1990 | Green |
| 4,991,764 | A | 2/1991 | Mericle |
| 5,014,899 | A | 5/1991 | Presty et al. |
| 5,031,814 | A | 7/1991 | Tompkins et al. |
| 5,040,715 | A | 8/1991 | Green et al. |
| 5,065,929 | A | 11/1991 | Schulze et al. |
| 5,071,430 | A | 12/1991 | de Salis et al. |
| 5,074,454 | A | 12/1991 | Peters |
| 5,083,695 | A | 1/1992 | Foslien et al. |
| 5,084,057 | A | 1/1992 | Green et al. |
| 5,106,008 | A | 4/1992 | Tompkins et al. |
| 5,111,987 | A | 5/1992 | Moeinzadeh et al. |
| 5,129,570 | A | 7/1992 | Schulze et al. |
| 5,141,144 | A | 8/1992 | Foslien et al. |
| 5,156,315 | A | 10/1992 | Green et al. |
| 5,156,614 | A | 10/1992 | Green et al. |
| 5,163,943 | A | 11/1992 | Mohiuddin et al. |
| 5,170,925 | A | 12/1992 | Madden et al. |
| 5,171,247 | A | 12/1992 | Hughett et al. |
| 5,173,133 | A | 12/1992 | Morin et al. |
| 5,180,092 | A | 1/1993 | Crainich |
| 5,188,274 | A | 2/1993 | Moeinzadeh et al. |
| 5,220,928 | A | 6/1993 | Oddsen et al. |
| 5,221,036 | A | 6/1993 | Takase |
| 5,242,457 | A | 9/1993 | Akopov et al. |
| 5,246,156 | A | 9/1993 | Rothfuss et al. |
| 5,253,793 | A | 10/1993 | Green et al. |
| 5,263,629 | A | 11/1993 | Trumbull et al. |
| RE34,519 | E | 1/1994 | Fox et al. |
| 5,275,323 | A | 1/1994 | Schulze et al. |
| 5,282,807 | A | 2/1994 | Knopfler |
| 5,289,963 | A | 3/1994 | McGarry et al. |
| 5,307,976 | A | 5/1994 | Olson et al. |
| 5,308,576 | A | 5/1994 | Green et al. |
| 5,312,023 | A | 5/1994 | Green et al. |
| 5,318,221 | A | 6/1994 | Green et al. |
| 5,326,013 | A | 7/1994 | Green et al. |
| 5,328,077 | A | 7/1994 | Lou |
| 5,330,486 | A | 7/1994 | Wilk |
| 5,332,142 | A | 7/1994 | Robinson et al. |
| 5,336,232 | A | 8/1994 | Green et al. |
| 5,344,061 | A | 9/1994 | Crainich |
| 5,352,238 | A | 10/1994 | Green et al. |
| 5,356,064 | A | 10/1994 | Green et al. |
| 5,358,506 | A | 10/1994 | Green et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,376,095 | A | 12/1994 | Ortiz |
| 5,379,933 | A | 1/1995 | Green et al. |
| 5,381,943 | A | 1/1995 | Allen et al. |
| 5,382,255 | A | 1/1995 | Castro et al. |
| 5,383,880 | A | 1/1995 | Hooven |
| 5,389,098 | A | 2/1995 | Tsuruta et al. |
| 5,395,033 | A | 3/1995 | Byrne et al. |
| 5,395,034 | A | 3/1995 | Allen et al. |
| 5,397,046 | A | 3/1995 | Savage et al. |
| 5,397,324 | A | 3/1995 | Carroll et al. |
| 5,403,312 | A | 4/1995 | Yates et al. |
| 5,405,072 | A | 4/1995 | Zlock et al. |
| 5,407,293 | A | 4/1995 | Crainich |
| 5,413,268 | A | 5/1995 | Green et al. |
| 5,415,334 | A | 5/1995 | Williamson et al. |
| 5,415,335 | A | 5/1995 | Knodell, Jr. |
| 5,417,361 | A | 5/1995 | Williamson, IV |
| 5,423,471 | A | 6/1995 | Mastri et al. |
| 5,425,745 | A | 6/1995 | Green et al. |
| 5,431,322 | A | 7/1995 | Green et al. |
| 5,431,323 | A | 7/1995 | Smith et al. |
| 5,433,721 | A | 7/1995 | Hooven et al. |
| 5,441,193 | A | 8/1995 | Gravener |
| 5,445,304 | A | 8/1995 | Plyley et al. |
| 5,447,265 | A | 9/1995 | Vidal et al. |
| 5,452,837 | A | 9/1995 | Williamson, IV et al. |
| 5,456,401 | A | 10/1995 | Green et al. |
| 5,464,300 | A | 11/1995 | Crainich |
| 5,465,895 | A | 11/1995 | Knodel et al. |
| 5,467,911 | A | 11/1995 | Tsuruta et al. |
| 5,470,007 | A | 11/1995 | Plyley et al. |
| 5,470,010 | A | 11/1995 | Rothfuss et al. |
| 5,472,132 | A | 12/1995 | Savage et al. |
| 5,474,566 | A | 12/1995 | Alesi et al. |
| 5,476,206 | A | 12/1995 | Green et al. |
| 5,478,003 | A | 12/1995 | Green et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,486,185 | A | 1/1996 | Freitas et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,856 | A | 2/1996 | Person et al. |
| 5,497,933 | A | 3/1996 | DeFonzo et al. |
| 5,501,689 | A | 3/1996 | Green et al. |
| 5,505,363 | A | 4/1996 | Green et al. |
| 5,507,426 | A | 4/1996 | Young et al. |
| 5,518,163 | A | 5/1996 | Hooven |
| 5,518,164 | A | 5/1996 | Hooven |
| 5,529,235 | A | 6/1996 | Boiarski et al. |
| 5,531,744 | A | 7/1996 | Nardella et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,542,594 | A | 8/1996 | McKean et al. |
| 5,549,628 | A | 8/1996 | Cooper et al. |
| 5,551,622 | A | 9/1996 | Yoon |
| 5,553,765 | A | 9/1996 | Knodel et al. |
| 5,554,164 | A | 9/1996 | Wilson et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,701 | A | 10/1996 | Huitema et al. |
| 5,564,615 | A | 10/1996 | Bishop et al. |
| 5,571,116 | A | 11/1996 | Bolanos et al. |
| 5,573,169 | A | 11/1996 | Green et al. |
| 5,573,543 | A | 11/1996 | Akopov et al. |
| 5,575,799 | A | 11/1996 | Bolanos et al. |
| 5,575,803 | A | 11/1996 | Cooper et al. |
| 5,577,654 | A | 11/1996 | Bishop |
| 5,584,425 | A | 12/1996 | Savage et al. |
| 5,586,711 | A | 12/1996 | Plyley et al. |
| 5,588,580 | A | 12/1996 | Paul et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,607,095 | A | 3/1997 | Smith et al. |
| 5,615,820 | A | 4/1997 | Viola |
| 5,618,291 | A | 4/1997 | Thompson et al. |
| 5,624,452 | A | 4/1997 | Yates |
| 5,626,587 | A | 5/1997 | Bishop et al. |
| 5,628,446 | A | 5/1997 | Geiste et al. |
| 5,630,539 | A | 5/1997 | Plyley et al. |
| 5,630,540 | A | 5/1997 | Blewett |

(56) References Cited

U.S. PATENT DOCUMENTS

| | | | |
|---|---|---|---|
| 5,630,541 | A | 5/1997 | Williamson, IV et al. |
| 5,632,432 | A | 5/1997 | Schulze et al. |
| 5,634,584 | A | 6/1997 | Okorocha et al. |
| 5,636,780 | A | 6/1997 | Green et al. |
| 5,645,209 | A | 7/1997 | Green et al. |
| 5,647,526 | A | 7/1997 | Green et al. |
| 5,651,491 | A | 7/1997 | Heaton et al. |
| 5,653,373 | A | 8/1997 | Green et al. |
| 5,653,374 | A | 8/1997 | Young et al. |
| 5,653,721 | A | 8/1997 | Knodel et al. |
| 5,655,698 | A | 8/1997 | Yoon |
| 5,657,921 | A | 8/1997 | Young et al. |
| 5,658,300 | A | 8/1997 | Bito et al. |
| 5,662,258 | A | 9/1997 | Knodel et al. |
| 5,662,259 | A | 9/1997 | Yoon |
| 5,662,260 | A | 9/1997 | Yoon |
| 5,662,662 | A | 9/1997 | Bishop et al. |
| 5,662,666 | A | 9/1997 | Onuki et al. |
| 5,665,085 | A | 9/1997 | Nardella |
| 5,667,517 | A | 9/1997 | Hooven |
| 5,669,544 | A | 9/1997 | Schulze et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,676,674 | A | 10/1997 | Bolanos et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,690,269 | A | 11/1997 | Bolanos et al. |
| 5,690,675 | A | 11/1997 | Sawyer et al. |
| 5,692,668 | A | 12/1997 | Schulze et al. |
| 5,697,542 | A | 12/1997 | Knodel et al. |
| 5,702,409 | A | 12/1997 | Rayburn et al. |
| 5,704,534 | A | 1/1998 | Huitema et al. |
| 5,706,997 | A | 1/1998 | Green et al. |
| 5,709,334 | A | 1/1998 | Sorrentino et al. |
| 5,711,472 | A | 1/1998 | Bryan |
| 5,713,505 | A | 2/1998 | Huitema |
| 5,715,988 | A | 2/1998 | Palmer |
| 5,716,366 | A | 2/1998 | Yates |
| 5,718,359 | A | 2/1998 | Palmer et al. |
| 5,725,536 | A | 3/1998 | Oberlin et al. |
| 5,725,554 | A | 3/1998 | Simon et al. |
| 5,728,110 | A | 3/1998 | Vidal et al. |
| 5,732,806 | A | 3/1998 | Foshee et al. |
| 5,735,848 | A | 4/1998 | Yates et al. |
| 5,743,456 | A | 4/1998 | Jones et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,256 | A | 6/1998 | Mastri et al. |
| 5,769,303 | A | 6/1998 | Knodel et al. |
| 5,769,892 | A | 6/1998 | Kingwell |
| 5,772,099 | A | 6/1998 | Gravener |
| 5,772,673 | A | 6/1998 | Cuny et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,834 | A | 7/1998 | Lucey et al. |
| 5,785,232 | A | 7/1998 | Vidal et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,811 | A | 9/1998 | Yates et al. |
| 5,810,855 | A | 9/1998 | Rayburn et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,109 | A | 10/1998 | McGarry et al. |
| 5,820,009 | A | 10/1998 | Melling et al. |
| 5,823,066 | A | 10/1998 | Huitema et al. |
| 5,826,776 | A | 10/1998 | Schulze et al. |
| 5,829,662 | A | 11/1998 | Allen et al. |
| 5,833,695 | A | 11/1998 | Yoon |
| 5,836,147 | A | 11/1998 | Schnipke |
| 5,862,972 | A | 1/1999 | Green et al. |
| 5,865,361 | A | 2/1999 | Milliman et al. |
| 5,871,135 | A | 2/1999 | Williamson, IV et al. |
| 5,873,873 | A | 2/1999 | Smith et al. |
| 5,878,938 | A | 3/1999 | Bittner et al. |
| 5,893,506 | A | 4/1999 | Powell |
| 5,894,979 | A | 4/1999 | Powell |
| 5,897,562 | A | 4/1999 | Bolanos et al. |
| 5,901,895 | A | 5/1999 | Heaton et al. |
| 5,911,352 | A | 6/1999 | Racenet et al. |
| 5,911,353 | A | 6/1999 | Bolanos et al. |
| 5,918,791 | A | 7/1999 | Sorrentino et al. |
| 5,919,198 | A | 7/1999 | Graves, Jr. et al. |
| 5,922,001 | A | 7/1999 | Yoon |
| 5,931,847 | A | 8/1999 | Bittner et al. |
| 5,941,442 | A | 8/1999 | Geiste et al. |
| 5,954,259 | A | 9/1999 | Viola et al. |
| 5,964,774 | A | 10/1999 | McKean et al. |
| 5,980,510 | A | 11/1999 | Tsonton et al. |
| 5,988,479 | A | 11/1999 | Palmer |
| 6,004,335 | A | 12/1999 | Vaitekunas et al. |
| 6,010,054 | A | 1/2000 | Johnson et al. |
| 6,032,849 | A | 3/2000 | Mastri et al. |
| 6,045,560 | A | 4/2000 | McKean et al. |
| 6,063,097 | A | 5/2000 | Oi et al. |
| 6,079,606 | A | 6/2000 | Milliman et al. |
| 6,099,551 | A | 8/2000 | Gabbay |
| 6,109,500 | A | 8/2000 | Alli et al. |
| 6,131,789 | A | 10/2000 | Schulze et al. |
| 6,131,790 | A | 10/2000 | Piraka |
| 6,155,473 | A | 12/2000 | Tompkins et al. |
| 6,197,017 | B1 | 3/2001 | Brock et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,279,809 | B1 | 8/2001 | Nicolo |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,391,038 | B2 | 5/2002 | Vargas et al. |
| 6,398,797 | B2 | 6/2002 | Bombard et al. |
| 6,436,097 | B1 | 8/2002 | Nardella |
| 6,439,446 | B1 | 8/2002 | Perry et al. |
| 6,443,973 | B1 | 9/2002 | Whitman |
| 6,478,804 | B2 | 11/2002 | Vargas et al. |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,602,252 | B2 | 8/2003 | Mollenauer |
| 6,619,529 | B2 | 9/2003 | Green et al. |
| D480,808 | S | 10/2003 | Wells et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,681,978 | B2 | 1/2004 | Geiste et al. |
| 6,698,643 | B2 | 3/2004 | Whitman |
| 6,716,232 | B1 | 4/2004 | Vidal et al. |
| 6,722,552 | B2 | 4/2004 | Fenton, Jr. |
| 6,755,338 | B2 | 6/2004 | Hahnen et al. |
| 6,783,524 | B2 | 8/2004 | Anderson et al. |
| 6,786,382 | B1 | 9/2004 | Hoffman |
| 6,817,509 | B2 | 11/2004 | Geiste et al. |
| 6,830,174 | B2 | 12/2004 | Hillstead et al. |
| 6,835,199 | B2 | 12/2004 | McGuckin, Jr. et al. |
| 6,843,403 | B2 | 1/2005 | Whitman |
| RE38,708 | E | 3/2005 | Bolanos et al. |
| 6,877,647 | B2 | 4/2005 | Green et al. |
| 6,889,116 | B2 | 5/2005 | Jinno |

(56) References Cited

U.S. PATENT DOCUMENTS 6,905,057 B2 6/2005 Swayze et al.
6,945,444 B2 9/2005 Gresham et al.
6,953,138 B1 10/2005 Dworak et al.
6,953,139 B2 10/2005 Milliman et al.
6,959,852 B2 11/2005 Shelton, IV et al.
6,962,594 B1 11/2005 Thevenet
6,964,363 B2 11/2005 Wales et al.
6,978,921 B2 12/2005 Shelton, IV et al.
6,981,628 B2 1/2006 Wales
6,986,451 B1 1/2006 Mastri et al.
6,988,649 B2 1/2006 Shelton, IV et al.
6,991,627 B2 1/2006 Madhani et al.
6,994,714 B2 2/2006 Vargas et al.
7,000,818 B2 2/2006 Shelton, IV et al.
7,000,819 B2 2/2006 Swayze et al.
7,032,799 B2 4/2006 Viola et al.
7,044,352 B2 5/2006 Shelton, IV et al.
7,044,353 B2 5/2006 Mastri et al.
7,055,730 B2 6/2006 Ehrenfels et al.
7,055,731 B2 6/2006 Shelton, IV et al.
7,059,508 B2 6/2006 Shelton, IV et al.
7,070,083 B2 7/2006 Jankowski
7,083,075 B2 8/2006 Swayze et al.
7,097,089 B2 8/2006 Marczyk
7,111,769 B2 9/2006 Wales et al.
7,114,642 B2 10/2006 Whitman
7,121,446 B2 10/2006 Arad et al.
7,128,253 B2 10/2006 Mastri et al.
7,128,254 B2 10/2006 Shelton, IV et al.
7,140,527 B2 11/2006 Ehrenfels et al.
7,140,528 B2 11/2006 Shelton, IV
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,147,138 B2 12/2006 Shelton, IV
7,159,750 B2 1/2007 Racenet et al.
7,168,604 B2 1/2007 Milliman et al.
7,172,104 B2 2/2007 Scirica et al.
7,188,758 B2 3/2007 Viola et al.
7,207,471 B2 4/2007 Heinrich et al.
7,213,736 B2 5/2007 Wales et al.
7,225,963 B2 6/2007 Scirica
7,225,964 B2 6/2007 Mastri et al.
7,238,195 B2 7/2007 Viola
7,246,734 B2 7/2007 Shelton, IV
7,258,262 B2 8/2007 Mastri et al.
7,267,682 B1 9/2007 Bender et al.
7,278,562 B2 10/2007 Mastri et al.
7,278,563 B1 10/2007 Green
7,287,682 B1 10/2007 Ezzat et al.
7,293,685 B2 11/2007 Ehrenfels et al.
7,296,722 B2 11/2007 Ivanko
7,296,724 B2 11/2007 Green et al.
7,296,772 B2 11/2007 Wang
7,300,444 B1 11/2007 Nielsen et al.
7,303,107 B2 12/2007 Milliman et al.
7,303,108 B2 12/2007 Shelton, IV
7,308,998 B2 12/2007 Mastri et al.
7,326,232 B2 2/2008 Viola et al.
7,328,828 B2 2/2008 Ortiz et al.
7,328,829 B2 2/2008 Arad et al.
7,334,717 B2 2/2008 Rethy et al.
7,354,447 B2 4/2008 Shelton, IV et al.
7,357,287 B2 4/2008 Shelton, IV et al.
7,364,061 B2 4/2008 Swayze et al.
7,367,485 B2 5/2008 Shelton, IV et al.
7,377,928 B2 5/2008 Zubik et al.
7,380,695 B2 6/2008 Doll et al.
7,380,696 B2 6/2008 Shelton, IV et al.
7,396,356 B2 7/2008 Mollenauer
7,398,907 B2 7/2008 Racenet et al.
7,399,310 B2 7/2008 Edoga et al.
7,401,720 B1 7/2008 Durrani
7,401,721 B2 7/2008 Holsten et al.
7,404,508 B2 7/2008 Smith et al.
7,404,509 B2 7/2008 Ortiz et al.
7,407,074 B2 8/2008 Ortiz et al.
7,407,075 B2 8/2008 Holsten et al.
7,407,077 B2 8/2008 Ortiz et al.
7,407,078 B2 8/2008 Shelton, IV et al.
7,416,101 B2 8/2008 Shelton, IV et al.
7,419,080 B2 9/2008 Smith et al.
7,419,081 B2 9/2008 Ehrenfels et al.
7,419,495 B2 9/2008 Menn et al.
7,422,139 B2 9/2008 Shelton, IV et al.
7,424,965 B2 9/2008 Racenet et al.
7,431,189 B2 10/2008 Shelton, IV et al.
7,431,730 B2 10/2008 Viola
7,434,715 B2 10/2008 Shelton, IV et al.
7,434,717 B2 10/2008 Shelton, IV et al.
7,438,208 B2 10/2008 Larson
7,438,209 B1 10/2008 Hess et al.
7,441,684 B2 10/2008 Shelton, IV et al.
7,441,685 B1 10/2008 Boudreaux
7,448,525 B2 11/2008 Shelton, IV et al.
7,451,904 B2 11/2008 Shelton, IV
7,455,208 B2 11/2008 Wales et al.
7,455,676 B2 11/2008 Holsten et al.
7,458,494 B2 12/2008 Matsutani et al.
7,461,767 B2 12/2008 Viola et al.
7,462,185 B1 12/2008 Knodel
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,472,814 B2 1/2009 Mastri et al.
7,472,815 B2 1/2009 Shelton, IV et al.
7,472,816 B2 1/2009 Holsten et al.
7,473,258 B2 1/2009 Clauson et al.
7,481,347 B2 1/2009 Roy
7,481,348 B2 1/2009 Marczyk
7,481,349 B2 1/2009 Holsten et al.
7,481,824 B2 1/2009 Boudreaux et al.
7,487,899 B2 2/2009 Shelton, IV et al.
7,490,749 B2 2/2009 Schall et al.
7,494,039 B2 2/2009 Racenet et al.
7,500,979 B2 3/2009 Hueil et al.
7,503,474 B2 3/2009 Hillstead et al.
7,506,790 B2 3/2009 Shelton, IV
7,506,791 B2 3/2009 Omaits et al.
7,510,107 B2 3/2009 Timm et al.
7,513,408 B2 4/2009 Shelton, IV et al.
7,517,356 B2 4/2009 Heinrich
7,537,602 B2 5/2009 Whitman
7,543,729 B2 6/2009 Ivanko
7,543,730 B1 6/2009 Marczyk
7,543,731 B2 6/2009 Green et al.
7,552,854 B2 6/2009 Wixey et al.
7,556,185 B2 7/2009 Viola
7,556,186 B2 7/2009 Milliman
7,559,450 B2 7/2009 Wales et al.
7,559,452 B2 7/2009 Wales et al.
7,559,453 B2 7/2009 Heinrich et al.
7,559,937 B2 7/2009 de la Torre et al.
7,565,993 B2 7/2009 Milliman et al.
7,568,603 B2 8/2009 Shelton, IV et al.
7,568,604 B2 8/2009 Ehrenfels et al.
7,571,845 B2 8/2009 Viola
7,575,144 B2 8/2009 Ortiz et al.
7,584,880 B2 9/2009 Racenet et al.
7,588,174 B2 9/2009 Holsten et al.
7,588,175 B2 9/2009 Timm et al.
7,588,176 B2 9/2009 Timm et al.
7,588,177 B2 9/2009 Racenet
7,597,229 B2 10/2009 Boudreaux et al.
7,597,230 B2 10/2009 Racenet et al.
7,600,663 B2 10/2009 Green
7,604,150 B2 10/2009 Boudreaux
7,604,151 B2 10/2009 Hess et al.
7,607,557 B2 10/2009 Shelton, IV et al.
7,611,038 B2 11/2009 Racenet et al.
7,617,961 B2 11/2009 Viola

(56) References Cited

U.S. PATENT DOCUMENTS 7,624,902 B2 12/2009 Marczyk et al.
7,624,903 B2 12/2009 Green et al.
7,631,793 B2 12/2009 Rethy et al.
7,631,794 B2 12/2009 Rethy et al.
7,635,073 B2 12/2009 Heinrich
7,635,074 B2 12/2009 Olson et al.
7,635,373 B2 12/2009 Ortiz
7,637,409 B2 12/2009 Marczyk
7,637,410 B2 12/2009 Marczyk
7,641,091 B2 1/2010 Olson et al.
7,641,095 B2 1/2010 Viola
7,644,848 B2 1/2010 Swayze et al.
7,648,055 B2 1/2010 Marczyk
7,651,017 B2 1/2010 Ortiz et al.
7,654,431 B2 2/2010 Hueil et al.
7,658,311 B2 2/2010 Boudreaux
7,658,312 B2 2/2010 Vidal et al.
7,665,646 B2 2/2010 Prommersberger
7,665,647 B2 2/2010 Shelton, IV et al.
7,669,746 B2 3/2010 Shelton, IV
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,678,121 B1 3/2010 Knodel
7,681,772 B2 3/2010 Green et al.
7,682,367 B2 3/2010 Shah et al.
7,682,368 B1 3/2010 Bombard et al.
7,690,547 B2 4/2010 Racenet et al.
7,694,865 B2 4/2010 Scirica
7,699,205 B2 4/2010 Ivanko
7,703,653 B2 4/2010 Shah et al.
7,721,931 B2 5/2010 Shelton, IV et al.
7,721,933 B2 5/2010 Ehrenfels et al.
7,721,935 B2 5/2010 Racenet et al.
7,726,537 B2 6/2010 Olson et al.
7,726,538 B2 6/2010 Holsten et al.
7,726,539 B2 6/2010 Holsten et al.
7,731,072 B2 6/2010 Timm et al.
7,735,703 B2 6/2010 Morgan et al.
7,740,159 B2 6/2010 Shelton, IV et al.
7,740,160 B2 6/2010 Viola
7,743,960 B2 6/2010 Whitman et al.
7,744,628 B2 6/2010 Viola
7,753,245 B2 7/2010 Boudreaux et al.
7,753,248 B2 7/2010 Viola
7,757,924 B2 7/2010 Gerbi et al.
7,757,925 B2 7/2010 Viola et al.
7,762,445 B2 7/2010 Heinrich et al.
7,766,209 B2 8/2010 Baxter, III et al.
7,766,210 B2 8/2010 Shelton, IV et al.
7,766,924 B1 8/2010 Bombard et al.
7,766,928 B2 8/2010 Ezzat et al.
7,770,774 B2 8/2010 Mastri et al.
7,770,775 B2 8/2010 Shelton, IV et al.
7,776,060 B2 8/2010 Mooradian et al.
7,780,055 B2 8/2010 Scirica et al.
7,784,662 B2 8/2010 Wales et al.
7,789,283 B2 9/2010 Shah
7,789,889 B2 9/2010 Zubik et al.
7,793,812 B2 9/2010 Moore et al.
7,793,814 B2 9/2010 Racenet et al.
7,794,475 B2 9/2010 Hess et al.
7,798,385 B2 9/2010 Boyden et al.
7,798,386 B2 9/2010 Schall et al.
7,799,039 B2 9/2010 Shelton, IV et al.
7,810,690 B2 10/2010 Bilotti et al.
7,810,692 B2 10/2010 Hall et al.
7,810,693 B2 10/2010 Broehl et al.
7,815,090 B2 10/2010 Marczyk
7,815,091 B2 10/2010 Marczyk
7,815,092 B2 10/2010 Whitman et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,896 B2 10/2010 Racenet
7,823,760 B2 11/2010 Zemlok et al.
7,823,761 B2 11/2010 Boyden et al.
7,824,426 B2 11/2010 Racenet et al.
7,828,186 B2 11/2010 Wales
7,828,187 B2 11/2010 Green et al.
7,828,188 B2 11/2010 Jankowski
7,828,189 B2 11/2010 Holsten et al.
7,832,408 B2 11/2010 Shelton, IV et al.
7,832,611 B2 11/2010 Boyden et al.
7,832,612 B2 11/2010 Baxter, III et al.
7,834,630 B2 11/2010 Damadian et al.
7,837,079 B2 11/2010 Holsten et al.
7,837,081 B2 11/2010 Holsten et al.
7,841,503 B2 11/2010 Sonnenschein et al.
7,845,533 B2 12/2010 Marczyk et al.
7,845,534 B2 12/2010 Viola et al.
7,845,535 B2 12/2010 Scircia
7,845,537 B2 12/2010 Shelton, IV et al.
7,845,538 B2 12/2010 Whitman
7,850,703 B2 12/2010 Bombard et al.
7,857,183 B2 12/2010 Shelton, IV
7,857,184 B2 12/2010 Viola
7,857,185 B2 12/2010 Swayze et al.
7,857,186 B2 12/2010 Baxter, III et al.
7,861,906 B2 1/2011 Doll et al.
7,861,907 B2 1/2011 Green et al.
7,866,524 B2 1/2011 Krehel
7,866,525 B2 1/2011 Scirica
7,866,526 B2 1/2011 Green et al.
7,866,527 B2 1/2011 Hall et al.
7,866,528 B2 1/2011 Olson et al.
7,870,989 B2 1/2011 Viola et al.
7,886,952 B2 2/2011 Scirica et al.
7,891,532 B2 2/2011 Mastri et al.
7,891,533 B2 2/2011 Green et al.
7,891,534 B2 2/2011 Wenchell et al.
7,896,214 B2 3/2011 Farascioni
7,900,805 B2 3/2011 Shelton, IV et al.
7,901,416 B2 3/2011 Nolan et al.
7,905,380 B2 3/2011 Shelton, IV et al.
7,905,381 B2 3/2011 Baxter, III et al.
7,909,039 B2 3/2011 Hur
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,543 B2 3/2011 Roth et al.
7,918,230 B2 4/2011 Whitman et al.
7,922,061 B2 4/2011 Shelton, IV et al.
7,922,063 B2 4/2011 Zemlok et al.
7,922,064 B2 4/2011 Boyden et al.
7,926,691 B2 4/2011 Viola et al.
7,926,692 B2 4/2011 Racenet et al.
7,934,628 B2 5/2011 Wenchell et al.
7,934,630 B2 5/2011 Shelton, IV et al.
7,934,631 B2 5/2011 Balbierz et al.
7,942,300 B2 5/2011 Rethy et al.
7,942,303 B2 5/2011 Shah
7,950,560 B2 5/2011 Zemlok et al.
7,950,561 B2 5/2011 Aranyi
7,950,562 B2 5/2011 Beardsley et al.
7,954,682 B2 6/2011 Giordano et al.
7,954,683 B1 6/2011 Knodel et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,959,051 B2 6/2011 Smith et al.
7,963,431 B2 6/2011 Scirica
7,963,432 B2 6/2011 Knodel et al.
7,963,433 B2 6/2011 Whitman et al.
7,967,178 B2 6/2011 Scirica et al.
7,967,179 B2 6/2011 Olson et al.
7,967,180 B2 6/2011 Scirica
7,975,894 B2 7/2011 Boyden et al.

(56) References Cited

U.S. PATENT DOCUMENTS

| | | | |
|---|---|---|---|
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,758 | B2 | 8/2011 | Whitman et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,887 | B2 | 8/2011 | Marczyk |
| 8,007,505 | B2 | 8/2011 | Weller et al. |
| 8,007,513 | B2 | 8/2011 | Nalagatla et al. |
| 8,011,550 | B2 | 9/2011 | Aranyi et al. |
| 8,011,551 | B2 | 9/2011 | Marczyk et al. |
| 8,011,552 | B2 | 9/2011 | Ivanko |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,015,976 | B2 | 9/2011 | Shah |
| 8,016,177 | B2 | 9/2011 | Bettuchi et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,882 | B2 | 10/2011 | Viola |
| 8,028,883 | B2 | 10/2011 | Stopek |
| 8,028,884 | B2 | 10/2011 | Sniffin et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, IV et al. |
| 8,167,186 | B2 | 5/2012 | Racenet et al. |
| 8,172,121 | B2 | 5/2012 | Krehel |
| 8,172,124 | B2 | 5/2012 | Shelton, IV et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,215,532 | B2 | 7/2012 | Marczyk |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 | 7/2012 | Farascioni et al. |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |
| 8,276,594 | B2 | 10/2012 | Shah |
| 8,276,801 | B2 | 10/2012 | Zemlok et al. |
| 8,281,973 | B2 | 10/2012 | Wenchell et al. |
| 8,286,847 | B2 | 10/2012 | Taylor |
| 8,286,848 | B2 | 10/2012 | Wenchell et al. |
| 8,286,850 | B2 | 10/2012 | Viola |
| 8,292,146 | B2 | 10/2012 | Holsten et al. |
| 8,292,147 | B2 | 10/2012 | Viola |
| 8,292,148 | B2 | 10/2012 | Viola |
| 8,292,149 | B2 | 10/2012 | Ivanko |
| 8,292,150 | B2 | 10/2012 | Bryant |
| 8,292,151 | B2 | 10/2012 | Viola |
| 8,292,152 | B2 | 10/2012 | Milliman et al. |
| 8,292,153 | B2 | 10/2012 | Jankowski |
| 8,292,154 | B2 | 10/2012 | Marczyk |
| 8,292,155 | B2 | 10/2012 | Shelton, IV et al. |
| 8,292,156 | B2 | 10/2012 | Kostrzewski |
| 8,292,158 | B2 | 10/2012 | Sapienza |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,044 | B2 | 11/2012 | Viola |
| 8,308,046 | B2 | 11/2012 | Prommersberger |
| 8,308,757 | B2 | 11/2012 | Hillstead et al. |
| 8,317,070 | B2 | 11/2012 | Hueil et al. |
| 8,317,071 | B1 | 11/2012 | Knodel |
| 8,322,455 | B2 | 12/2012 | Shelton, IV et al. |
| 8,322,589 | B2 | 12/2012 | Boudreaux |
| 8,328,061 | B2 | 12/2012 | Kasvikis |

(56) References Cited

U.S. PATENT DOCUMENTS

| | | | |
|---|---|---|---|
| 8,328,065 | B2 | 12/2012 | Shah |
| 8,333,313 | B2 | 12/2012 | Boudreaux et al. |
| 8,336,751 | B2 | 12/2012 | Scirica |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,353,437 | B2 | 1/2013 | Boudreaux |
| 8,353,440 | B2 | 1/2013 | Whitman et al. |
| 8,356,740 | B1 | 1/2013 | Knodel |
| 8,357,174 | B2 | 1/2013 | Roth et al. |
| 8,360,294 | B2 | 1/2013 | Scirica |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,365,971 | B1 | 2/2013 | Knodel |
| 8,365,972 | B2 | 2/2013 | Aranyi et al. |
| 8,365,973 | B1 | 2/2013 | White et al. |
| 8,365,976 | B2 | 2/2013 | Hess et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,381,828 | B2 | 2/2013 | Whitman et al. |
| 8,381,961 | B2 | 2/2013 | Holsten et al. |
| 8,387,848 | B2 | 3/2013 | Johnson et al. |
| 8,387,849 | B2 | 3/2013 | Buesseler et al. |
| 8,387,850 | B2 | 3/2013 | Hathaway et al. |
| 8,388,652 | B2 | 3/2013 | Viola |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,397,971 | B2 | 3/2013 | Yates et al. |
| 8,397,972 | B2 | 3/2013 | Kostrzewski |
| 8,403,195 | B2 | 3/2013 | Beardsley et al. |
| 8,403,196 | B2 | 3/2013 | Beardsley et al. |
| 8,403,197 | B2 | 3/2013 | Vidal et al. |
| 8,403,198 | B2 | 3/2013 | Sorrentino et al. |
| 8,403,956 | B1 | 3/2013 | Thompson et al. |
| 8,408,439 | B2 | 4/2013 | Huang et al. |
| 8,408,440 | B2 | 4/2013 | Olson et al. |
| 8,408,442 | B2 | 4/2013 | Racenet et al. |
| 8,413,868 | B2 | 4/2013 | Cappola |
| 8,413,869 | B2 | 4/2013 | Heinrich |
| 8,413,871 | B2 | 4/2013 | Racenet et al. |
| 8,418,904 | B2 | 4/2013 | Wenchell et al. |
| 8,418,905 | B2 | 4/2013 | Milliman |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,419,768 | B2 | 4/2013 | Marczyk |
| 8,424,735 | B2 | 4/2013 | Viola et al. |
| 8,424,736 | B2 | 4/2013 | Scirica et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,439,244 | B2 | 5/2013 | Holcomb et al. |
| 8,439,245 | B2 | 5/2013 | Knodel et al. |
| 8,439,246 | B1 | 5/2013 | Knodel |
| 8,444,036 | B2 | 5/2013 | Shelton, IV |
| 8,444,037 | B2 | 5/2013 | Nicholas et al. |
| 8,444,038 | B2 | 5/2013 | Farascioni et al. |
| 8,448,832 | B2 | 5/2013 | Viola et al. |
| 8,453,652 | B2 | 6/2013 | Stopek |
| 8,453,905 | B2 | 6/2013 | Holcomb et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,909 | B2 | 6/2013 | Olson et al. |
| 8,453,910 | B2 | 6/2013 | Bettuchi et al. |
| 8,453,912 | B2 | 6/2013 | Mastri et al. |
| 8,453,913 | B2 | 6/2013 | Milliman |
| 8,453,914 | B2 | 6/2013 | Laurent et al. |
| 8,454,628 | B2 | 6/2013 | Smith et al. |
| 8,459,520 | B2 | 6/2013 | Giordano et al. |
| 8,459,521 | B2 | 6/2013 | Zemlok et al. |
| 8,459,522 | B2 | 6/2013 | Marczyk |
| 8,459,523 | B2 | 6/2013 | Whitman |
| 8,459,524 | B2 | 6/2013 | Pribanic et al. |
| 8,459,525 | B2 | 6/2013 | Yates et al. |
| 8,464,922 | B2 | 6/2013 | Marczyk |
| 8,464,923 | B2 | 6/2013 | Shelton, IV |
| 8,469,252 | B2 | 6/2013 | Holcomb et al. |
| 8,469,254 | B2 | 6/2013 | Czernik et al. |
| 8,474,677 | B2 | 7/2013 | Woodard, Jr. et al. |
| 8,479,967 | B2 | 7/2013 | Marczyk |
| 8,479,968 | B2 | 7/2013 | Hodgkinson et al. |
| 8,479,969 | B2 | 7/2013 | Shelton, IV |
| 8,485,412 | B2 | 7/2013 | Shelton, IV et al. |
| 8,490,852 | B2 | 7/2013 | Viola |
| 8,496,152 | B2 | 7/2013 | Viola |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,499,993 | B2 | 8/2013 | Shelton, IV et al. |
| 8,505,799 | B2 | 8/2013 | Viola et al. |
| 8,505,802 | B2 | 8/2013 | Viola et al. |
| 8,511,575 | B2 | 8/2013 | Cok |
| 8,512,359 | B2 | 8/2013 | Whitman et al. |
| 8,512,402 | B2 | 8/2013 | Marczyk et al. |
| 8,517,240 | B1 | 8/2013 | Mata et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,523,041 | B2 | 9/2013 | Ishitsuki et al. |
| 8,523,042 | B2 | 9/2013 | Masiakos et al. |
| 8,523,043 | B2 | 9/2013 | Ullrich et al. |
| 8,534,528 | B2 | 9/2013 | Shelton, IV |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,733 | B2 | 9/2013 | Whitman et al. |
| 8,544,711 | B2 | 10/2013 | Ma et al. |
| 8,550,325 | B2 | 10/2013 | Cohen et al. |
| 8,556,151 | B2 | 10/2013 | Viola |
| 8,561,870 | B2 | 10/2013 | Baxter, III et al. |
| 8,561,873 | B2 | 10/2013 | Ingmanson et al. |
| 8,561,874 | B2 | 10/2013 | Scirica |
| 8,567,656 | B2 | 10/2013 | Shelton, IV et al. |
| 8,573,461 | B2 | 11/2013 | Shelton, IV et al. |
| 8,573,463 | B2 | 11/2013 | Scirica et al. |
| 8,573,465 | B2 | 11/2013 | Shelton, IV |
| 8,579,176 | B2 | 11/2013 | Smith et al. |
| 8,579,177 | B2 | 11/2013 | Beetel |
| 8,584,919 | B2 | 11/2013 | Hueil et al. |
| 8,584,920 | B2 | 11/2013 | Hodgkinson |
| 8,590,762 | B2 | 11/2013 | Hess et al. |
| 8,596,515 | B2 | 12/2013 | Okoniewski |
| 8,597,311 | B2 | 12/2013 | Criscuolo et al. |
| 8,602,288 | B2 | 12/2013 | Shelton, IV et al. |
| 8,608,045 | B2 | 12/2013 | Smith et al. |
| 8,608,046 | B2 | 12/2013 | Laurent et al. |
| 8,608,047 | B2 | 12/2013 | Holsten et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,430 | B2 | 12/2013 | (Prommersberger) Stopek et al. |
| 8,627,994 | B2 | 1/2014 | Zemlok et al. |
| 8,628,544 | B2 | 1/2014 | Farascioni |
| 8,631,988 | B2 | 1/2014 | Viola |
| 8,631,989 | B2 | 1/2014 | Aranyi et al. |
| 8,631,991 | B2 | 1/2014 | Cropper et al. |
| 8,632,525 | B2 | 1/2014 | Kerr et al. |
| 8,632,535 | B2 | 1/2014 | Shelton, IV et al. |

(56) References Cited

U.S. PATENT DOCUMENTS 8,636,187 B2 1/2014 Hueil et al.
8,636,190 B2 1/2014 Zemlok et al.
8,636,192 B2 1/2014 Farascioni et al.
8,636,762 B2 1/2014 Whitman et al.
8,636,766 B2 1/2014 Milliman et al.
8,640,940 B2 2/2014 Ohdaira
8,657,174 B2 2/2014 Yates et al.
8,657,177 B2 2/2014 Scirica et al.
8,657,178 B2 2/2014 Hueil et al.
8,662,371 B2 3/2014 Viola
8,668,129 B2 3/2014 Olson
8,672,206 B2 3/2014 Aranyi et al.
8,672,208 B2 3/2014 Hess et al.
8,672,209 B2 3/2014 Crainich
8,678,263 B2 3/2014 Viola
8,678,990 B2 3/2014 Wazer et al.
8,679,155 B2 3/2014 Knodel et al.
8,684,247 B2 4/2014 Scirica et al.
8,684,249 B2 4/2014 Racenet et al.
8,684,253 B2 4/2014 Giordano et al.
8,690,039 B2 4/2014 Beardsley et al.
8,695,865 B2 4/2014 Smith et al.
8,695,866 B2 4/2014 Leimbach et al.
8,701,958 B2 4/2014 Shelton, IV et al.
8,701,959 B2 4/2014 Shah
8,701,961 B2 4/2014 Ivanko
8,708,213 B2 4/2014 Shelton, IV et al.
8,714,429 B2 5/2014 Demmy
8,715,277 B2 5/2014 Weizman
8,720,766 B2 5/2014 Hess et al.
8,721,630 B2 5/2014 Ortiz et al.
8,727,197 B2 5/2014 Hess et al.
8,727,200 B2 5/2014 Roy
8,733,612 B2 5/2014 Ma
8,740,034 B2 6/2014 Morgan et al.
8,740,039 B2 6/2014 Farascioni
8,746,529 B2 6/2014 Shelton, IV et al.
8,746,530 B2 6/2014 Giordano et al.
8,746,533 B2 6/2014 Whitman
8,746,534 B2 6/2014 Farascioni
8,746,535 B2 6/2014 Shelton, IV et al.
8,747,421 B2 6/2014 Balbierz et al.
8,752,747 B2 6/2014 Shelton, IV et al.
8,752,748 B2 6/2014 Whitman et al.
8,752,749 B2 6/2014 Moore et al.
8,757,465 B2 6/2014 Woodard, Jr. et al.
8,758,391 B2 6/2014 Swayze et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,770,458 B2 7/2014 Scirica
8,777,082 B2 7/2014 Scirica
8,783,541 B2 7/2014 Shelton, IV et al.
8,783,542 B2 7/2014 Riestenberg et al.
8,789,737 B2 7/2014 Hodgkinson et al.
8,789,738 B2 7/2014 Knodel et al.
8,789,739 B2 7/2014 Swensgard
8,800,838 B2 8/2014 Shelton, IV
8,800,840 B2 8/2014 Jankowski
8,800,841 B2 8/2014 Ellerhorst et al.
8,808,311 B2 8/2014 Heinrich et al.
8,814,024 B2 8/2014 Woodard, Jr. et al.
8,814,025 B2 8/2014 Miller et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,827,133 B2 9/2014 Shelton, IV et al.
8,827,134 B2 9/2014 Viola et al.
8,833,631 B2 9/2014 Munro, III et al.
8,833,632 B2 9/2014 Swensgard
8,840,003 B2 9/2014 Morgan et al.
8,840,603 B2 9/2014 Shelton, IV et al.
8,844,788 B2 9/2014 Knodel
8,851,354 B2 10/2014 Swensgard et al.
8,851,355 B2 10/2014 Aranyi et al.
8,857,693 B2 10/2014 Schuckmann et al.
8,864,007 B2 10/2014 Widenhouse et al.
8,864,009 B2 10/2014 Shelton, IV et al.
8,864,010 B2 10/2014 Williams
8,870,050 B2 10/2014 Hodgkinson
8,875,971 B2 11/2014 Hall et al.
8,875,972 B2 11/2014 Weisenburgh, II et al.
8,893,949 B2 11/2014 Shelton, IV et al.
8,893,950 B2 11/2014 Marczyk
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,900,616 B2 12/2014 Belcheva et al.
8,920,435 B2 12/2014 Smith et al.
8,925,782 B2 1/2015 Shelton, IV
8,926,598 B2 1/2015 Mollere et al.
8,931,681 B2 1/2015 Kostrzewski
8,931,682 B2 1/2015 Timm et al.
8,931,693 B1 1/2015 Kumar et al.
8,955,732 B2 2/2015 Zemlok et al.
8,958,429 B2 2/2015 Shukla et al.
8,960,517 B2 2/2015 Lee
8,960,520 B2 2/2015 McCuen
8,967,443 B2 3/2015 McCuen
8,967,446 B2 3/2015 Beardsley et al.
8,973,803 B2 3/2015 Hall et al.
8,978,954 B2 3/2015 Shelton, IV et al.
8,978,956 B2 3/2015 Schall et al.
8,991,677 B2 3/2015 Moore et al.
8,991,678 B2 3/2015 Wellman et al.
8,998,058 B2 4/2015 Moore et al.
8,998,060 B2 4/2015 Bruewer et al.
9,005,230 B2 4/2015 Yates et al.
9,010,606 B2 4/2015 Aranyi et al.
9,010,607 B2 4/2015 Kostrzewski
9,010,610 B2 4/2015 Hodgkinson
9,016,539 B2 4/2015 Kostrzewski et al.
9,016,541 B2 4/2015 Viola et al.
9,016,542 B2 4/2015 Shelton, IV et al.
9,016,544 B2 4/2015 Hodgkinson et al.
9,016,545 B2 4/2015 Aranyi et al.
9,016,546 B2 4/2015 Demmy et al.
9,017,371 B2 4/2015 Whitman et al.
9,022,271 B2 5/2015 Scirica
9,027,817 B2 5/2015 Milliman et al.
9,033,203 B2 5/2015 Woodard, Jr. et al.
9,044,228 B2 6/2015 Woodard, Jr. et al.
9,044,229 B2 6/2015 Scheib et al.
9,050,084 B2 6/2015 Schmid et al.
9,055,941 B2 6/2015 Schmid et al.
9,060,770 B2 6/2015 Shelton, IV et al.
9,072,535 B2 7/2015 Shelton, IV et al.
9,084,601 B2 7/2015 Moore et al.
9,084,602 B2 7/2015 Gleiman
9,089,326 B2 7/2015 Krumanaker et al.
9,095,339 B2 8/2015 Moore et al.
9,101,359 B2 8/2015 Smith et al.
9,107,663 B2 8/2015 Swensgard
9,107,664 B2 8/2015 Marczyk
9,107,667 B2 8/2015 Hodgkinson
9,113,862 B2 8/2015 Morgan et al.
9,113,864 B2 8/2015 Morgan et al.
9,113,870 B2 8/2015 Viola
9,113,872 B2 8/2015 Viola
9,113,880 B2 8/2015 Zemlok et al.
9,125,649 B2 9/2015 Bruewer et al.
9,138,225 B2 9/2015 Huang et al.
9,155,537 B2 10/2015 Katre et al.
9,179,912 B2 11/2015 Yates et al.
9,192,378 B2 11/2015 Aranyi et al.
9,192,379 B2 11/2015 Aranyi et al.
9,192,384 B2 11/2015 Bettuchi
9,198,644 B2 12/2015 Balek et al.
9,198,660 B2 12/2015 Hodgkinson
9,198,661 B2 12/2015 Swensgard
9,198,662 B2 12/2015 Barton et al.

(56) References Cited

U.S. PATENT DOCUMENTS 9,204,876 B2 12/2015 Cappola et al.
9,204,877 B2 12/2015 Whitman et al.
9,204,880 B2 12/2015 Baxter, III et al.
9,216,019 B2 12/2015 Schmid et al.
9,216,020 B2 12/2015 Zhang et al.
9,220,500 B2 12/2015 Swayze et al.
9,220,501 B2 12/2015 Baxter, III et al.
9,220,502 B2 12/2015 Zemlok et al.
9,232,941 B2 1/2016 Mandakolathur Vasudevan et al.
9,232,944 B2 1/2016 Cappola et al.
9,237,891 B2 1/2016 Shelton, IV
9,237,892 B2 1/2016 Hodgkinson
9,254,180 B2 2/2016 Huitema et al.
9,265,585 B2 2/2016 Wingardner et al.
9,271,728 B2 3/2016 Gupta et al.
9,272,406 B2 3/2016 Aronhalt et al.
9,277,919 B2 3/2016 Timmer et al.
9,282,962 B2 3/2016 Schmid et al.
9,283,054 B2 3/2016 Morgan et al.
9,289,209 B2 3/2016 Gurumurthy et al.
9,289,210 B2 3/2016 Baxter, III et al.
9,289,225 B2 3/2016 Shelton, IV et al.
9,295,464 B2 3/2016 Shelton, IV et al.
9,295,465 B2 3/2016 Farascioni
9,295,466 B2 3/2016 Hodgkinson et al.
9,301,752 B2 4/2016 Mandakolathur Vasudevan et al.
9,301,753 B2 4/2016 Aldridge et al.
9,301,757 B2 4/2016 Williams
9,301,759 B2 4/2016 Spivey et al.
9,307,965 B2 4/2016 Ming et al.
9,307,986 B2 4/2016 Hall et al.
9,307,989 B2 4/2016 Shelton, IV et al.
9,314,246 B2 4/2016 Shelton, IV et al.
9,320,518 B2 4/2016 Henderson et al.
9,320,521 B2 4/2016 Shelton, IV et al.
9,320,523 B2 4/2016 Shelton, IV et al.
9,326,767 B2 5/2016 Koch, Jr. et al.
9,326,771 B2 5/2016 Baxter, III et al.
9,332,987 B2 5/2016 Leimbach et al.
9,345,477 B2 5/2016 Anim et al.
9,345,478 B2 5/2016 Knodel
9,345,479 B2 5/2016 (Tarinelli) Racenet et al.
9,345,481 B2 5/2016 Hall et al.
9,345,780 B2 5/2016 Manoharan et al.
9,351,726 B2 5/2016 Leimbach
9,351,727 B2 5/2016 Leimbach et al.
9,351,732 B2 5/2016 Hodgkinson
9,358,003 B2 6/2016 Hall et al.
9,364,217 B2 6/2016 Kostrzewski et al.
9,364,218 B2 6/2016 Scirica
9,364,219 B2 6/2016 Olson et al.
9,364,220 B2 6/2016 Williams
9,364,227 B2 6/2016 Kostrzewski
9,364,231 B2 6/2016 Wenchell
9,364,233 B2 6/2016 Alexander, III et al.
9,370,358 B2 6/2016 Shelton, IV et al.
9,370,362 B2 6/2016 Petty et al.
9,386,983 B2 7/2016 Swensgard et al.
9,386,984 B2 7/2016 Aronhalt et al.
9,386,988 B2 7/2016 Baxter, III et al.
9,393,018 B2 7/2016 Wang et al.
9,398,911 B2 7/2016 Auld
9,402,604 B2 8/2016 Williams et al.
9,402,627 B2 8/2016 Stevenson et al.
9,421,014 B2 8/2016 Ingmanson et al.
9,433,419 B2 9/2016 Gonzalez et al.
9,433,420 B2 9/2016 Hodgkinson
9,445,810 B2 9/2016 Cappola
9,445,813 B2 9/2016 Shelton, IV et al.
9,451,959 B2 9/2016 Patankar et al.
9,468,438 B2 10/2016 Baber et al.
9,468,439 B2 10/2016 Cappola et al.
9,480,476 B2 11/2016 Aldridge et al.
9,480,492 B2 11/2016 Aranyi et al.
9,492,171 B2 11/2016 Patenaude
9,498,212 B2 11/2016 Racenet et al.
9,498,219 B2 11/2016 Moore et al.
9,510,827 B2 12/2016 Kostrzewski
9,517,065 B2 12/2016 Simms et al.
9,517,066 B2 12/2016 Racenet et al.
9,522,002 B2 12/2016 Chowaniec et al.
9,539,007 B2 1/2017 Dhakad et al.
9,549,735 B2 1/2017 Shelton, IV et al.
9,554,794 B2 1/2017 Baber
9,561,029 B2 2/2017 Scheib et al.
9,561,031 B2 2/2017 Heinrich et al.
9,566,065 B2 2/2017 Knodel
9,572,576 B2 2/2017 Hodgkinson et al.
9,579,101 B2 2/2017 Whitman et al.
9,585,657 B2 3/2017 Shelton, IV et al.
9,585,662 B2 3/2017 Shelton, IV et al.
9,597,077 B2 3/2017 Hodgkinson
9,610,080 B2 4/2017 Whitfield et al.
9,615,825 B2 4/2017 Viola
9,615,826 B2 4/2017 Shelton, IV et al.
9,622,746 B2 4/2017 Simms
9,629,623 B2 4/2017 Lytle, IV et al.
9,629,626 B2 4/2017 Soltz et al.
9,629,628 B2 4/2017 Aranyi
9,629,629 B2 4/2017 Leimbach et al.
9,642,620 B2 5/2017 Baxter, III
9,649,109 B2 5/2017 Ranucci et al.
9,655,613 B2 5/2017 Schaller
9,662,108 B2 5/2017 Williams
9,668,728 B2 6/2017 Williams et al.
9,668,732 B2 6/2017 Patel et al.
9,675,351 B2 6/2017 Hodgkinson et al.
9,681,870 B2 6/2017 Baxter, III et al.
9,687,230 B2 6/2017 Leimbach et al.
9,687,233 B2 6/2017 Fernandez et al.
9,693,772 B2 7/2017 Ingmanson et al.
9,693,815 B2 7/2017 Motai
9,700,309 B2 7/2017 Jaworek
9,700,319 B2 7/2017 Motooka et al.
9,706,993 B2 7/2017 Hessler et al.
9,713,474 B2 7/2017 Lorenz
9,717,497 B2 8/2017 Zerkle et al.
9,717,498 B2 8/2017 Aranyi et al.
9,724,092 B2 8/2017 Baxter, III et al.
9,724,095 B2 8/2017 Gupta et al.
9,757,128 B2 9/2017 Baber et al.
9,763,662 B2 9/2017 Shelton, IV et al.
9,770,245 B2 9/2017 Swayze et al.
9,775,610 B2 10/2017 Nicholas et al.
9,775,635 B2 10/2017 Takei
9,782,169 B2 10/2017 Kimsey
9,782,173 B2 10/2017 Mozdzierz
9,795,379 B2 10/2017 Leimbach et al.
9,795,384 B2 10/2017 Weaner et al.
9,808,246 B2 11/2017 Shelton, IV
9,808,248 B2 11/2017 Hoffman
9,808,249 B2 11/2017 Shelton, IV
9,820,741 B2 11/2017 Kostrzewski
9,820,742 B2 11/2017 Covach et al.
9,827,002 B2 11/2017 Hausen et al.
9,839,420 B2 12/2017 Shelton, IV
9,839,421 B2 12/2017 Zerkle et al.
9,839,428 B2 12/2017 Baxter, III et al.
9,855,038 B2 1/2018 Smith et al.
9,855,040 B2 1/2018 Kostrzewski
9,861,358 B2 1/2018 Marczyk et al.
9,861,359 B2 1/2018 Shelton, IV et al.
9,867,612 B2 1/2018 Parihar et al.
9,867,613 B2 1/2018 Marczyk et al.
9,867,615 B2 1/2018 Fanelli et al.
9,872,683 B2 1/2018 Hopkins
9,883,860 B2 2/2018 Leimbach et al.
9,901,342 B2 2/2018 Shelton, IV et al.
9,913,646 B2 3/2018 Shelton, IV
9,918,714 B2 3/2018 Gibbons, Jr.
9,918,717 B2 3/2018 Czernik
9,924,941 B2 3/2018 Burbank
9,924,942 B2 3/2018 Swayze et al.
9,936,951 B2 4/2018 Hufnagel et al.

(56) References Cited

U.S. PATENT DOCUMENTS

| | | | |
|---|---|---|---|
| 9,936,954 | B2 | 4/2018 | Shelton, IV et al. |
| 9,943,311 | B2 | 4/2018 | Scirica et al. |
| 9,949,737 | B2 | 4/2018 | Zergiebel et al. |
| 9,955,966 | B2 | 5/2018 | Zergiebel |
| 9,968,354 | B2 | 5/2018 | Shelton, IV et al. |
| 9,980,724 | B2 | 5/2018 | Farascioni et al. |
| 9,987,012 | B2 | 6/2018 | Shah |
| 9,987,099 | B2 | 6/2018 | Chen et al. |
| 9,993,248 | B2 | 6/2018 | Shelton, IV et al. |
| 9,993,258 | B2 | 6/2018 | Shelton, IV et al. |
| 10,004,497 | B2 | 6/2018 | Overmyer et al. |
| 10,004,505 | B2 | 6/2018 | Moore et al. |
| 10,034,668 | B2 | 7/2018 | Ebner |
| 10,039,532 | B2 | 8/2018 | Srinivas et al. |
| 10,039,545 | B2 | 8/2018 | Sadowski et al. |
| 10,045,782 | B2 | 8/2018 | Murthy Aravalli |
| 10,052,044 | B2 | 8/2018 | Shelton, IV et al. |
| 10,058,963 | B2 | 8/2018 | Shelton, IV et al. |
| 10,064,622 | B2 | 9/2018 | Murthy Aravalli |
| 10,076,325 | B2 | 9/2018 | Huang et al. |
| 10,085,750 | B2 | 10/2018 | Zergiebel et al. |
| 10,092,290 | B2 | 10/2018 | Yigit et al. |
| 10,092,292 | B2 | 10/2018 | Boudreaux et al. |
| 10,111,657 | B2 | 10/2018 | McCuen |
| 10,111,665 | B2 | 10/2018 | Aranyi |
| 10,117,650 | B2 | 11/2018 | Nicholas et al. |
| 10,117,654 | B2 | 11/2018 | Ingmanson et al. |
| 10,123,796 | B2 | 11/2018 | Westling et al. |
| 10,123,798 | B2 | 11/2018 | Baxter, III et al. |
| 10,135,242 | B2 | 11/2018 | Baber et al. |
| 10,143,474 | B2 | 12/2018 | Bucciaglia et al. |
| 10,172,612 | B2 | 1/2019 | Frushour |
| 10,172,615 | B2 | 1/2019 | Marczyk et al. |
| 10,172,617 | B2 | 1/2019 | Shelton, IV et al. |
| 10,175,127 | B2 | 1/2019 | Collins et al. |
| 10,180,463 | B2 | 1/2019 | Beckman et al. |
| 10,182,816 | B2 | 1/2019 | Shelton, IV et al. |
| 10,206,677 | B2 | 2/2019 | Harris et al. |
| 10,213,201 | B2 | 2/2019 | Shelton, IV et al. |
| 10,219,804 | B2 | 3/2019 | Linder et al. |
| 10,226,239 | B2 | 3/2019 | Nicholas et al. |
| 10,226,250 | B2 | 3/2019 | Beckman et al. |
| 10,226,254 | B2 | 3/2019 | Cabrera et al. |
| 10,245,033 | B2 | 4/2019 | Overmyer et al. |
| 10,245,038 | B2 | 4/2019 | Hopkins et al. |
| 10,251,725 | B2 | 4/2019 | Valentine et al. |
| 10,265,065 | B2 | 4/2019 | Shelton, IV et al. |
| 10,265,066 | B2 | 4/2019 | Measamer et al. |
| 10,265,074 | B2 | 4/2019 | Shelton, IV et al. |
| 10,271,840 | B2 | 4/2019 | Sapre |
| 10,271,841 | B2 | 4/2019 | Overmyer et al. |
| 10,285,694 | B2 | 5/2019 | Viola et al. |
| 10,285,698 | B2 | 5/2019 | Cappola et al. |
| 10,285,700 | B2 | 5/2019 | Scheib |
| 10,321,907 | B2 | 6/2019 | Shelton, IV et al. |
| 10,327,776 | B2 | 6/2019 | Harris et al. |
| 10,335,150 | B2 | 7/2019 | Shelton, IV |
| 10,349,939 | B2 | 7/2019 | Shelton, IV et al. |
| 10,349,941 | B2 | 7/2019 | Marczyk et al. |
| 10,368,867 | B2 | 8/2019 | Harris et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,405,857 | B2 | 9/2019 | Shelton |
| 10,426,468 | B2 | 10/2019 | Contini et al. |
| 10,441,279 | B2 | 10/2019 | Shelton, IV et al. |
| 10,456,129 | B2 | 10/2019 | Shelton, IV et al. |
| 10,456,130 | B2 | 10/2019 | Cheney et al. |
| 10,463,368 | B2 | 11/2019 | Kostrzewski |
| 10,470,762 | B2 | 11/2019 | Leimbach et al. |
| 10,470,911 | B2 | 11/2019 | Thompson et al. |
| 10,478,182 | B2 | 11/2019 | Taylor |
| 10,478,183 | B2 | 11/2019 | Hess et al. |
| 10,478,187 | B2 | 11/2019 | Shelton, IV et al. |
| 10,542,976 | B2 | 1/2020 | Calderoni et al. |
| 10,548,504 | B2 | 2/2020 | Shelton, IV et al. |
| 10,548,593 | B2 | 2/2020 | Shelton, IV et al. |
| 10,548,599 | B2 | 2/2020 | Marczyk et al. |
| 10,561,417 | B2 | 2/2020 | Zergiebel et al. |
| 10,561,418 | B2 | 2/2020 | Richard et al. |
| 10,568,621 | B2 | 2/2020 | Shelton, IV et al. |
| 10,588,629 | B2 | 3/2020 | Malinouskas et al. |
| 10,595,929 | B2 | 3/2020 | Boudreaux et al. |
| 10,603,128 | B2 | 3/2020 | Zergiebel et al. |
| 10,610,224 | B2 | 4/2020 | Shelton, IV et al. |
| 10,617,412 | B2 | 4/2020 | Shelton, IV et al. |
| 10,624,634 | B2 | 4/2020 | Shelton, IV et al. |
| 10,675,026 | B2 | 6/2020 | Harris et al. |
| 10,687,806 | B2 | 6/2020 | Shelton, IV et al. |
| 10,695,053 | B2 | 6/2020 | Hess et al. |
| 10,729,434 | B2 | 8/2020 | Harris et al. |
| 10,765,424 | B2 | 9/2020 | Baxter, III et al. |
| 10,779,822 | B2 | 9/2020 | Yates et al. |
| 10,792,038 | B2 | 10/2020 | Becerra et al. |
| 10,828,030 | B2 | 11/2020 | Weir et al. |
| 10,863,984 | B2 | 12/2020 | Shelton, IV et al. |
| 10,905,420 | B2 | 2/2021 | Jasemian et al. |
| 10,905,422 | B2 | 2/2021 | Bakos et al. |
| 10,959,726 | B2 | 3/2021 | Williams et al. |
| 11,064,999 | B2 | 7/2021 | Nelson et al. |
| 11,090,051 | B2 | 8/2021 | Kostrzewski |
| 11,207,065 | B2 | 12/2021 | Harris et al. |
| 11,213,294 | B2 | 1/2022 | Shelton, IV et al. |
| 11,266,409 | B2 | 3/2022 | Huitema et al. |
| 11,278,288 | B2 | 3/2022 | Rector et al. |
| 11,439,391 | B2 | 9/2022 | Bruns et al. |
| 11,564,684 | B2 | 1/2023 | Harris et al. |
| 2004/0108357 | A1 | 6/2004 | Milliman et al. |
| 2004/0199180 | A1 | 10/2004 | Knodel et al. |
| 2004/0199181 | A1 | 10/2004 | Knodel et al. |
| 2004/0243151 | A1 | 12/2004 | Demmy et al. |
| 2004/0267310 | A1 | 12/2004 | Racenet et al. |
| 2005/0216055 | A1 | 9/2005 | Scirica et al. |
| 2006/0049229 | A1 | 3/2006 | Milliman et al. |
| 2006/0180634 | A1 | 8/2006 | Shelton et al. |
| 2006/0289602 | A1 | 12/2006 | Wales et al. |
| 2007/0073341 | A1 | 3/2007 | Smith et al. |
| 2007/0084897 | A1 | 4/2007 | Shelton et al. |
| 2007/0102472 | A1 | 5/2007 | Shelton |
| 2007/0106317 | A1 | 5/2007 | Shelton et al. |
| 2007/0119901 | A1 | 5/2007 | Ehrenfels et al. |
| 2007/0145096 | A1 | 6/2007 | Viola et al. |
| 2007/0170225 | A1 | 7/2007 | Shelton et al. |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0194079 | A1 | 8/2007 | Hueil et al. |
| 2007/0194082 | A1 | 8/2007 | Morgan et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0078802 | A1 | 4/2008 | Hess et al. |
| 2008/0110961 | A1 | 5/2008 | Voegele et al. |
| 2008/0169328 | A1 | 7/2008 | Shelton |
| 2008/0169332 | A1 | 7/2008 | Shelton et al. |
| 2008/0169333 | A1 | 7/2008 | Shelton et al. |
| 2008/0287987 | A1 | 11/2008 | Boyden et al. |
| 2008/0296346 | A1 | 12/2008 | Shelton, IV et al. |
| 2008/0308602 | A1 | 12/2008 | Timm et al. |
| 2008/0308603 | A1 | 12/2008 | Shelton et al. |
| 2009/0001121 | A1 | 1/2009 | Hess et al. |
| 2009/0001130 | A1 | 1/2009 | Hess et al. |
| 2009/0090763 | A1 | 4/2009 | Zemlok et al. |
| 2009/0090766 | A1 | 4/2009 | Knodel |
| 2009/0242610 | A1 | 10/2009 | Shelton, IV et al. |
| 2009/0255974 | A1 | 10/2009 | Viola |
| 2009/0308907 | A1 | 12/2009 | Nalagatla et al. |
| 2010/0012703 | A1 | 1/2010 | Calabrese et al. |
| 2010/0065604 | A1 | 3/2010 | Weng |
| 2010/0069942 | A1 | 3/2010 | Shelton, IV |
| 2010/0127041 | A1 | 5/2010 | Morgan et al. |
| 2010/0133317 | A1 | 6/2010 | Shelton, IV et al. |
| 2010/0147921 | A1 | 6/2010 | Olson |

(56) References Cited

U.S. PATENT DOCUMENTS

2010/0147922 A1 6/2010 Olson
2010/0155453 A1 6/2010 Bombard et al.
2010/0193566 A1 8/2010 Scheib et al.
2010/0224668 A1 9/2010 Fontayne et al.
2010/0249802 A1 9/2010 May et al.
2010/0252611 A1 10/2010 Ezzat et al.
2011/0006101 A1 1/2011 Hall et al.
2011/0024477 A1 2/2011 Hall
2011/0024478 A1 2/2011 Shelton, IV
2011/0036891 A1 2/2011 Zemlok et al.
2011/0087276 A1 4/2011 Bedi et al.
2011/0101069 A1 5/2011 Bombard et al.
2011/0147433 A1 6/2011 Shelton, IV et al.
2011/0163146 A1 7/2011 Ortiz et al.
2011/0192882 A1 8/2011 Hess et al.
2011/0278343 A1 11/2011 Knodel et al.
2011/0290853 A1* 12/2011 Shelton, IV ..... A61B 17/07207 227/177.1
2011/0290856 A1 12/2011 Shelton, IV et al.
2012/0053406 A1 3/2012 Conlon et al.
2012/0061446 A1 3/2012 Knodel et al.
2012/0074200 A1 3/2012 Schmid et al.
2012/0080478 A1 4/2012 Morgan et al.
2012/0080495 A1 4/2012 Holcomb et al.
2012/0080498 A1 4/2012 Shelton, IV et al.
2012/0091183 A1 4/2012 Manoux et al.
2012/0138659 A1 6/2012 Marczyk et al.
2012/0193394 A1 8/2012 Holcomb et al.
2012/0193399 A1 8/2012 Holcomb et al.
2012/0211542 A1 8/2012 Racenet
2012/0234895 A1 9/2012 O'Connor et al.
2012/0234897 A1 9/2012 Shelton, IV et al.
2012/0241504 A1 9/2012 Soltz et al.
2012/0248169 A1 10/2012 Widenhouse et al.
2012/0286022 A1 11/2012 Olson et al.
2012/0298722 A1 11/2012 Hess et al.
2013/0008937 A1 1/2013 Viola
2013/0012983 A1 1/2013 Kleyman
2013/0020375 A1 1/2013 Shelton, IV et al.
2013/0020376 A1 1/2013 Shelton, IV et al.
2013/0026208 A1 1/2013 Shelton, IV et al.
2013/0026210 A1 1/2013 Shelton, IV et al.
2013/0041406 A1 2/2013 Bear et al.
2013/0068816 A1 3/2013 Mandakolathur Vasudevan et al.
2013/0068818 A1 3/2013 Kasvikis
2013/0075447 A1 3/2013 Weisenburgh, II et al.
2013/0098970 A1 4/2013 Racenet et al.
2013/0153641 A1 6/2013 Shelton, IV et al.
2013/0175316 A1 7/2013 Thompson et al.
2013/0256380 A1 10/2013 Schmid et al.
2013/0277410 A1 10/2013 Fernandez et al.
2013/0334280 A1 12/2013 Krehel et al.
2014/0014704 A1 1/2014 Onukuri et al.
2014/0014707 A1 1/2014 Onukuri et al.
2014/0048580 A1 2/2014 Merchant et al.
2014/0166724 A1 6/2014 Schellin et al.
2014/0166725 A1 6/2014 Schellin et al.
2014/0166726 A1 6/2014 Schellin et al.
2014/0175150 A1 6/2014 Shelton, IV et al.
2014/0239047 A1 8/2014 Hodgkinson et al.
2014/0246475 A1 9/2014 Hall et al.
2014/0252064 A1 9/2014 Mozdzierz et al.
2014/0263541 A1 9/2014 Leimbach et al.
2014/0263552 A1 9/2014 Hall et al.
2014/0263558 A1 9/2014 Hausen et al.
2014/0284371 A1 9/2014 Morgan et al.
2014/0291379 A1 10/2014 Schellin et al.
2014/0291383 A1 10/2014 Spivey et al.
2014/0367445 A1 12/2014 Ingmanson et al.
2015/0076211 A1 3/2015 Irka et al.
2015/0134076 A1 5/2015 Shelton, IV et al.
2015/0173749 A1 6/2015 Shelton, IV et al.
2015/0173756 A1 6/2015 Baxter, III et al.
2015/0250474 A1 9/2015 Abbott et al.
2015/0272557 A1 10/2015 Overmyer et al.
2015/0297222 A1 10/2015 Huitema et al.
2015/0297225 A1 10/2015 Huitema et al.
2015/0374372 A1 12/2015 Zergiebel et al.
2016/0166249 A1 6/2016 Knodel
2016/0166253 A1 6/2016 Knodel
2016/0235494 A1 8/2016 Shelton, IV et al.
2016/0302791 A1 10/2016 Schmitt
2016/0354176 A1 12/2016 Schmitt
2017/0000483 A1 1/2017 Motai et al.
2021/0077102 A1 3/2021 Williams

FOREIGN PATENT DOCUMENTS

CA 2884962 A1 11/2015
DE 2744824 A1 4/1978
DE 2903159 A1 7/1980
DE 3114135 A1 10/1982
DE 4213426 A1 10/1992
DE 4300307 A1 7/1994
EP 0041022 A1 12/1981
EP 0136950 A2 4/1985
EP 0140552 A2 5/1985
EP 0156774 A2 10/1985
EP 0213817 A1 3/1987
EP 0216532 A1 4/1987
EP 0220029 A1 4/1987
EP 0273468 A2 7/1988
EP 0324166 A2 7/1989
EP 0324635 A1 7/1989
EP 0324637 A1 7/1989
EP 0324638 A1 7/1989
EP 0365153 A1 4/1990
EP 0369324 A1 5/1990
EP 0373762 A1 6/1990
EP 0380025 A2 8/1990
EP 0399701 A1 11/1990
EP 0449394 A2 10/1991
EP 0484677 A1 5/1992
EP 0489436 A1 6/1992
EP 0503662 A1 9/1992
EP 0514139 A2 11/1992
EP 0536903 A2 4/1993
EP 0537572 A2 4/1993
EP 0539762 A1 5/1993
EP 0541950 A1 5/1993
EP 0545029 A1 6/1993
EP 0552050 A2 7/1993
EP 0552423 A2 7/1993
EP 0579038 A1 1/1994
EP 0589306 A2 3/1994
EP 0591946 A1 4/1994
EP 0592243 A2 4/1994
EP 0593920 A1 4/1994
EP 0598202 A1 5/1994
EP 0598579 A1 5/1994
EP 0600182 A2 6/1994
EP 0621006 A1 10/1994
EP 0621009 A1 10/1994
EP 0656188 A2 6/1995
EP 0666057 A2 8/1995
EP 0705571 A1 4/1996
EP 0760230 A1 3/1997
EP 1952769 A2 8/2008
EP 2090253 A2 8/2009
EP 2090254 A1 8/2009
EP 2583630 A2 4/2013
EP 2586382 A2 5/2013
EP 2907456 A1 8/2015
EP 3138509 A1 3/2017
EP 3338660 A1 6/2018
FR 391239 A 10/1908
FR 2542188 A1 9/1984
FR 2660851 A1 10/1991
FR 2681775 A1 4/1993
GB 1352554 A 5/1974
GB 1452185 A 10/1976
GB 1555455 A 11/1979
GB 2048685 A 12/1980
GB 2070499 A 9/1981

(56) References Cited

FOREIGN PATENT DOCUMENTS

| | | | |
|---|---|---|---|
| GB | 2141066 | A | 12/1984 |
| GB | 2165559 | A | 4/1986 |
| JP | 51149985 | | 12/1976 |
| JP | 2001087272 | | 4/2001 |
| JP | 2013215572 | A | 10/2013 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004032760 | A2 | 4/2004 |
| WO | 2009071070 | A2 | 6/2009 |
| WO | 2015191887 | A1 | 12/2015 |
| WO | 2018161313 | A1 | 9/2018 |
| WO | 2019186434 | A1 | 10/2019 |

* cited by examiner

SURGICAL STAPLING DEVICE WITH JAWS THAT PIVOT BETWEEN AN OPEN POSITION AND A CLAMPED POSITION

CROSS-REFERENCE TO RELATED APPLICATIONS

This application claims the benefit of U.S. Provisional Patent Application Ser. No. 63/464,992, filed May 9, 2023, the entire content of which is incorporated herein by reference.

FIELD

This disclosure is directed to surgical stapling devices, and more particularly, to surgical stapling devices including jaws that pivot between an open position and a clamped position.

BACKGROUND

Various types of surgical devices to endoscopically treat tissue are known in the art, and are commonly used, for example, for closure of tissue or organs in transection, resection, and anastomoses procedures, for occlusion of organs in thoracic and abdominal procedures, and for electrosurgically fusing or scaling tissue.

One example of such a surgical device is a stapling device. The stapling device includes an adapter assembly and a tool assembly supported on a distal portion of the adapter assembly. The tool assembly includes a first jaw that supports an anvil and a second jaw that supports a cartridge assembly. In some stapling devices, the anvil is fixedly supported on the anvil, or a mounting structure secured to the anvil, and the cartridge assembly is pivotally supported on the anvil, or a mounting structure secured to the anvil, such that the cartridge assembly can pivot in relation to the anvil between an open position and a clamped position. In some devices, the cartridge assembly is urged towards the open position by a biasing member.

Stapling devices configured for endoscopic or laparoscopic use are also known in the art. Such stapling devices are inserted through small incisions in the skin of a patient, or through small diameter cannulas, to access a surgical site within the patient. Typically, a clinician will use a tapered end of the cartridge assembly when the tool assembly is in the open position to dissect tissue within the body of the patient to access the surgical site. Since the cartridge assembly is not fixedly secured to the adapter assembly during the dissection of tissue, the cartridge assembly may not perform as desired.

A continuing need exists in the art for a stapling device that includes a cartridge assembly that can pivot in relation to the anvil between open and clamped positions while providing a rigid structure for dissecting tissue during positioning of the tool assembly at the surgical site.

SUMMARY

This application is directed to a surgical stapling device that includes an adapter assembly, a tool assembly supported on the distal portion of the adapter assembly, and a drive assembly that is movable in relation to the tool assembly to actuate the tool assembly. The tool assembly includes an anvil and a cartridge assembly that is pivotably coupled to the anvil for movement between an open position and a clamped position. The cartridge assembly includes a staple cartridge and a channel member that defines a cavity that receives the staple cartridge. The channel member supports a channel lock that is positioned on a proximal portion of the channel member. The drive assembly is movable from a drive advanced position to a drive retracted position and engages the channel lock in the drive retracted position to retain the tool assembly in the open position.

One aspect of this disclosure is directed to a tool assembly including an anvil, a cartridge assembly, and a drive assembly. The cartridge assembly includes a channel member, a staple cartridge, and a channel lock. The channel member is pivotably coupled to the anvil and movable in relation to the anvil between open and clamped positions. The channel member includes a proximal portion and has side walls and a bottom wall. The bottom wall defines a first knife slot and extends between the side walls to define a cavity. The staple cartridge is receivable within the cavity and includes a cartridge body, staples, and an actuation sled. The cartridge body defines a second knife slot and staple receiving slots positioned on opposite sides of the second knife slot. The actuation sled is movable within the cartridge body from a sled advanced position to a sled retracted position to eject the staples from the cartridge body. The channel lock is secured to the proximal portion of the channel member. The drive assembly includes a drive member and a working end. The drive member is movable between a drive retracted position and a drive advanced position to move the actuation sled from the sled retracted position to the sled advanced position. In the drive retracted position, the drive assembly is engaged with the channel lock to retain the channel member of the cartridge assembly in the open position.

In aspects of the disclosure, the channel lock is secured to the bottom wall of the channel member and extends between the side walls of the channel member.

In some aspects of the disclosure, the working end of the drive assembly has an I-beam configuration and includes a first beam, a second beam, and a strut interconnecting the first beam and the second beam.

In certain aspects of the disclosure, the first beam is positioned to engage the anvil and the second beam is positioned to engage the cartridge assembly when the drive assembly is moved from the drive retracted position towards the drive advanced position.

In aspects of the disclosure, the second beam is positioned to engage the channel lock when the drive assembly is in the drive retracted position.

In some aspects of the disclosure, the vertical strut includes a cutting blade.

In certain aspects of the disclosure, the channel lock has a circular cross-section and is secured to the bottom wall of the channel member.

In aspects of the disclosure, the channel lock has a linear portion with bent ends, and the channel member defines openings that receive the bent ends of the channel lock.

In some aspects of the disclosure, the bottom wall of the channel member includes a proximal portion that defines a cutout that communicates with the first knife slot.

In certain aspects of the disclosure, the working member of the drive assembly is received within the cutout when the drive assembly is in the drive retracted position.

In aspects of the disclosure, the channel lock is positioned proximally of the working member when the drive assembly is in the drive retracted position.

Other aspects of the disclosure are directed to a cartridge assembly including a channel member and a staple cartridge. The channel member includes a proximal portion and has side walls and a bottom wall. The bottom wall defines a first knife slot and extends between the side walls to define a cavity. The staple cartridge is receivable within the cavity and includes a cartridge body, staples, and an actuation sled. The cartridge body defines a second knife slot and staple receiving slots positioned on opposite sides of the second knife slot. The actuation sled is movable within the cartridge body from a sled advanced position to a sled retracted position to eject the staples from the cartridge body. The channel lock is secured to the proximal portion of the channel member and extends between the side walls of the channel member.

Still other aspects of the disclosure are directed to a channel assembly of a cartridge assembly for a surgical stapling device, the channel assembly including a channel member and a channel lock. The channel member includes a proximal portion and has side walls and a bottom wall. The bottom wall defines a first knife slot and extends between the side walls to define a cavity. The channel lock is secured to the proximal portion of the channel member and extends between the side walls of the channel member.

Other features of the disclosure will be appreciated from the following description.

BRIEF DESCRIPTION OF THE DRAWINGS

Various aspects of the disclosed surgical stapling device are described herein below with reference to the drawings, wherein.

DETAILED DESCRIPTION

Figure 1:
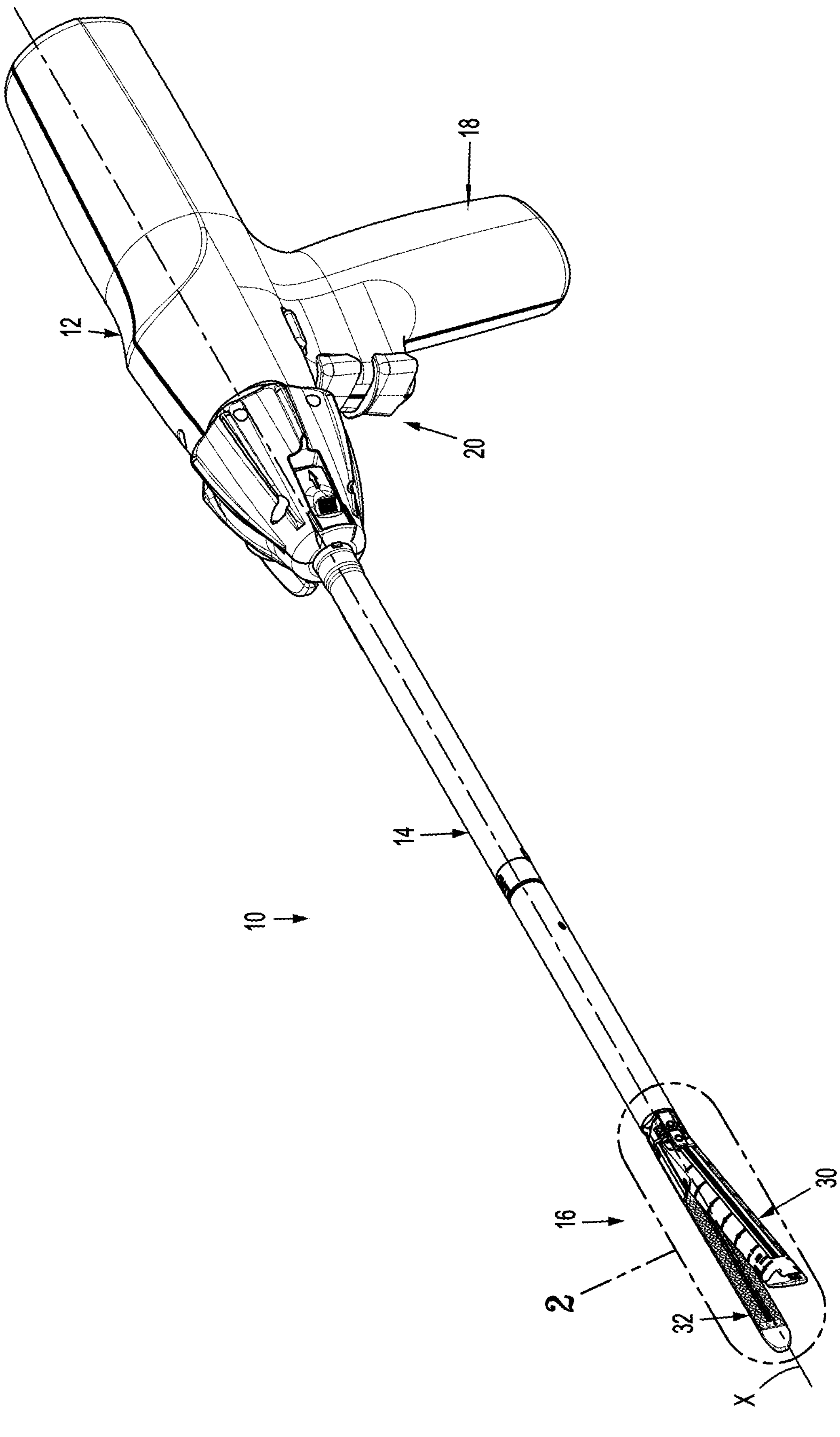
FIG. 1 is a side perspective view of a surgical stapling device according to aspects of this disclosure with a tool assembly in an open position.

The disclosed surgical stapling device will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

As used herein, the term "distal" refers to the portion of the stapling device that is being described which is further from a user during use of the device in its customary manner, while the term "proximal" refers to the portion of the stapling device that is being described which is closer to a user during use of the device in its customary manner. In addition, directional terms such as front, rear, upper, lower, top, bottom, and similar terms are used to assist in understanding the description and are not intended to limit the disclosure, and the term "clinician" is used generally to refer to medical personnel including doctors, nurses, surgeons, and support personnel.

This application is directed to a surgical stapling device that includes an adapter assembly, a tool assembly supported on the distal portion of the adapter assembly, and a drive assembly that is movable in relation to the tool assembly to actuate the tool assembly. The tool assembly includes an anvil and a cartridge assembly that is pivotably coupled to the anvil for movement between an open position and a clamped position. The cartridge assembly includes a staple cartridge and a channel member that defines a cavity that receives the staple cartridge. The channel member supports a channel lock that is positioned on a proximal portion of the channel member. The drive assembly is movable from a drive advanced position to a drive retracted position and engages the channel lock in the drive retracted position to retain the tool assembly in the open position.

Figure 2:
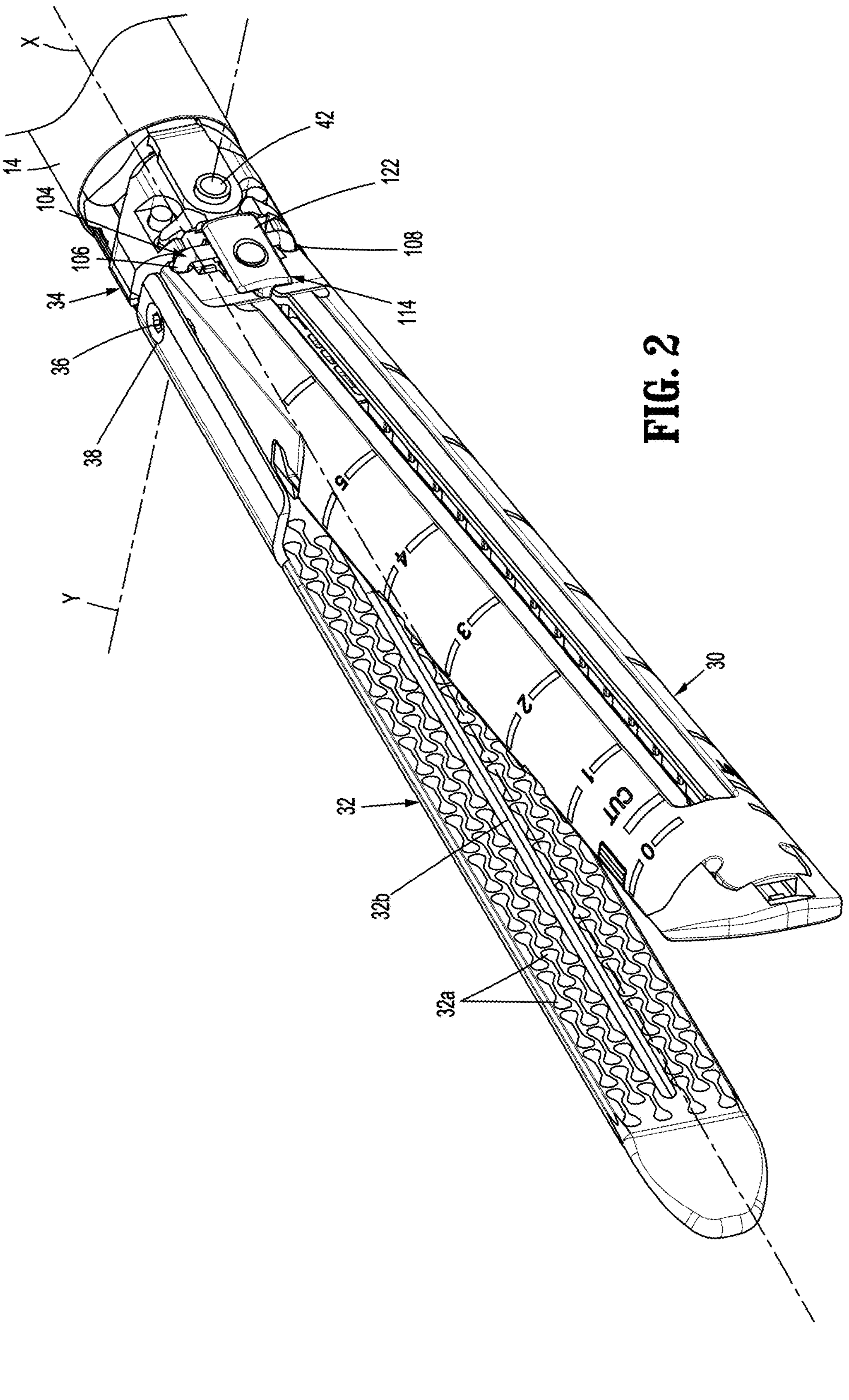
FIG. 2 is an enlarged view of the indicated area of detail shown in FIG. 1.

FIGS. 1 and 2 illustrate a surgical stapling device shown generally as stapling device 10 that includes a handle assembly 12, an elongate body or adapter assembly 14, and a tool assembly 16. As illustrated, the handle assembly 12 is powered and includes a stationary handgrip 18 and actuation buttons 20. The actuation buttons 20 are operable to actuate various functions of the tool assembly 16 via the adapter assembly 14 including approximation, stapling, cutting, and articulation. In certain aspects of the disclosure, the handle assembly 12 supports batteries (not shown) that provide power to the handle assembly 12 to operate the stapling device 10. Although the stapling device 10 is illustrated as a powered stapling device, it is envisioned that the features of this disclosure are suitable for use with manually powered surgical stapling devices as well as robotically controlled stapling devices.

Figure 2A:
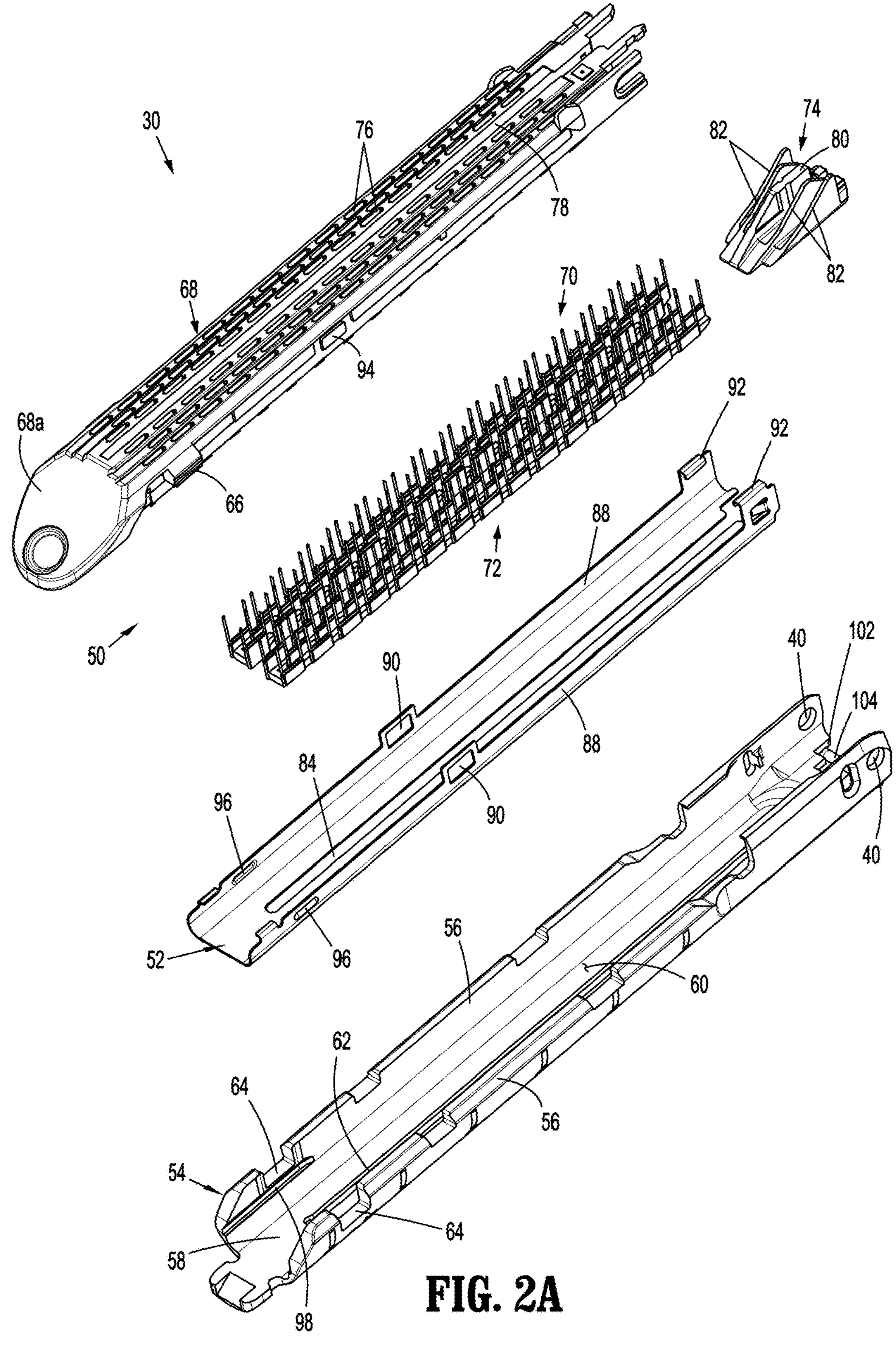
FIG. 2A is an exploded perspective view of a cartridge assembly of the tool assembly shown in FIG. 2.

The tool assembly 16 of the stapling device 10 includes a cartridge assembly 30 and an anvil 32. The anvil 32 includes a forming surface that defines staple forming pockets 32*a* and a knife slot 32*b*. In aspects of the disclosure, the tool assembly 16 is coupled to the adapter assembly 14 by a mounting assembly 34 (FIG. 2). In aspects of the disclosure, the proximal portion of the anvil 32 defines openings 38 (FIG. 2) and the proximal portion of the cartridge assembly 30 defines openings 40 (FIG. 2A). Screws 36 are received within the openings 38 of the anvil and in the mounting assembly 34 to fixedly secure the anvil 32 to the mounting assembly 34, and the screws 36 are received within the openings 40 of the cartridge assembly 30 to pivotably secure the cartridge assembly 30 to the mounting assembly 34 and the anvil 32 to facilitate movement of the tool assembly 16 between an open position and a clamped position.

In aspects of the disclosure, the mounting assembly 34 is secured to the distal portion of the adapter assembly 14 by a pivot member 42 that defines an articulation axis "Y" that is transverse to a longitudinal axis "X" (FIG. 1) defined by the adapter assembly 14 to pivotably secure the tool assembly 16 to the distal portion of the adapter assembly 14. It is envisioned that aspects of this disclosure are suitable for use with stapling devices that include non-articulating tool assemblies.

FIG. 2A illustrates the cartridge assembly 30 which includes a staple cartridge 50 having a staple guard 52, and a channel member 54. The channel member 54 includes side walls 56 and a bottom wall 58 that together define a cavity 60 that receives the staple cartridge 50. The bottom wall 58 of the channel member 54 defines a knife slot 62 that extends from the proximal end of the channel member 54 to a position near a distal end of the channel member 54. In aspects of the disclosure, the side walls 56 of the channel member include cut outs 64 that receive protrusions 66 formed on the staple cartridge 50 to properly position the staple cartridge 50 within the cavity 60 of the channel member 54.

The staple cartridge 50 includes a cartridge body 68, staples 70, pushers 72, and an actuation sled 74. The cartridge body 68 defines a plurality of staple receiving slots 76 and a knife slot 78 that is aligned with the knife slot 62 in the channel member 54 when the staple cartridge 50 is received within the cavity 60 of the channel member 54. A distal portion of the cartridge body 68 includes an angled surface 68*a* that defines a plane that extends away from the anvil 32 in a distal direction. In aspects of the disclosure, the staple receiving slots 76 are aligned in rows on opposite sides of the knife slot 78 although other arrays of staple receiving slots 76 are envisioned. Each of the staple receiving slots 76 receives one of the staples 70 and one of the pushers 72. The actuation sled 74 includes a central body portion 80 and cam members 82 that are positioned on opposite sides of the central body portion 80. The central body portion 80 is received within the knife slot 78 of the cartridge body 68 to guide movement of the actuation sled 74 through the cartridge body 68 from a sled retracted position to a sled advanced position. As the actuation sled 74 is moved from the sled retracted position towards the sled advanced position, the cam members 82 move into sequential engagement with the pushers 72 to eject the staples 70 from the cartridge body 68.

The staple guard 52 is secured to a bottom of the cartridge body 68 of the staple cartridge 50 to retain the staples 70 and the pushers 72 within the cartridge body 68 during shipping and handling of the staple cartridge 50. The staple guard 52 is positioned between the cartridge body 68 and the bottom wall 58 of the channel member 54 when the staple cartridge 50 is received within the cavity 60 of the channel member 54 and defines a knife slot 84 that is aligned with the knife slot 62 of the of the channel member 54 and the knife slot 78 of the cartridge body 68. In aspects of the disclosure, the staple guard 52 includes side walls 88 that define centrally located openings 90 and support proximally located hooks 92. The openings 90 receive protrusions 94 formed on the cartridge body 68 to secure the staple guard 52 to the cartridge body 68. Similarly, the hooks 92 engage a proximal portion of the cartridge body 68 to secure the staple guard 52 to the cartridge body 68. In some aspects of the disclosure, the staple guard 52 also includes distally located ribs 96 that extend outwardly from the side walls 88 of the staple guard 52 into channels 98 defined in the inner surfaces of the side walls 56 of the channel member 54 to releasably retain the staple cartridge 50 within the cavity 60 of the channel member 54. The staple cartridge 50 is releasably retained within the cavity 60 of the channel member 54 to facilitate replacement of the staple cartridge 50 and reuse the stapling device 10.

Figure 3:
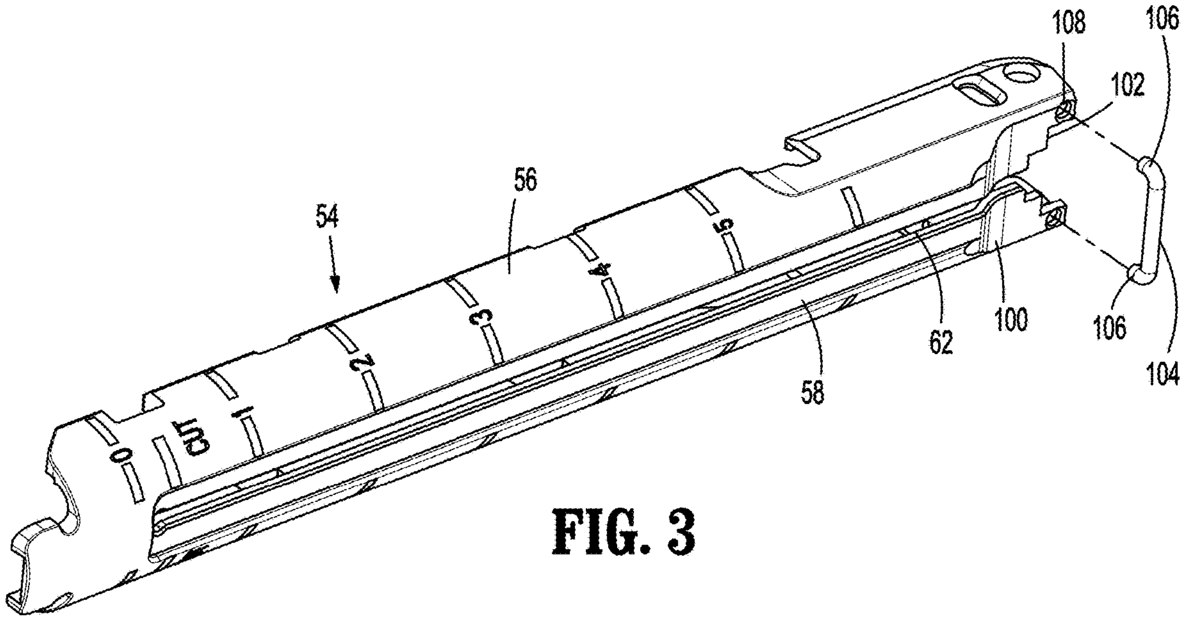
FIG. 3 is an exploded view of a channel member of the cartridge assembly shown in FIG. 2A.
Figure 4:
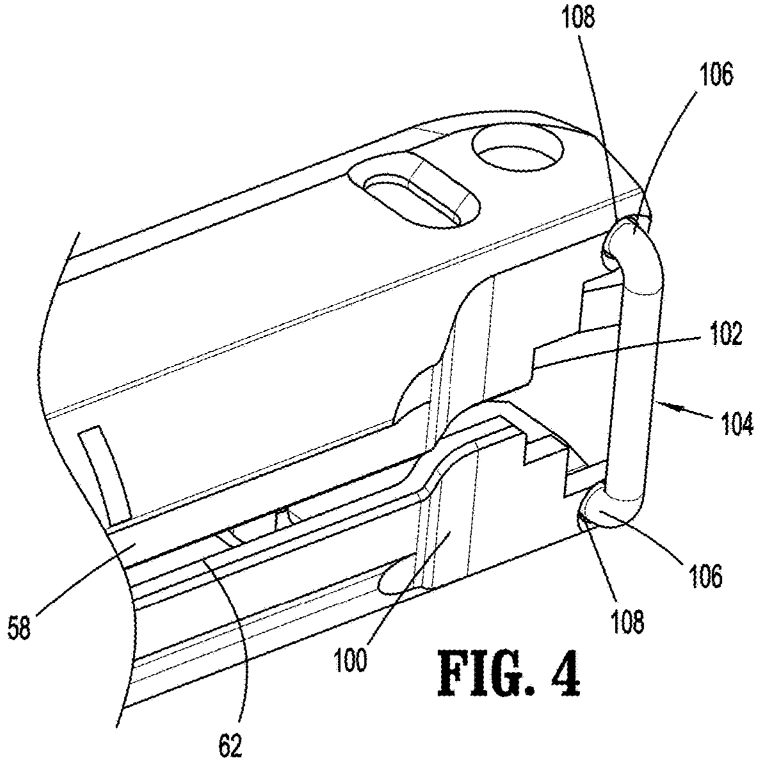
FIG. 4 is a side perspective view of a proximal portion of the channel member shown in FIG. 3.

FIGS. 3 and 4 illustrate the channel member 54 of the cartridge assembly 30 (FIG. 2A) of the stapling device 10 (FIG. 1). The bottom wall 58 of the channel member 54 has an outer surface that defines a ramp 100 that is positioned on the proximal portion of the channel member 54. The bottom wall 58 also defines a cutout 102 that communicates with the knife slot 62 and is positioned proximally of the ramp 100. In aspects of the disclosure, the cutout 102 has a stepped rectangular configuration although other cutout configurations are envisioned. The proximal portion of the channel member 54 supports a channel lock 104 that extends between the side walls 56 of the channel member 54 across the proximal portion of the cutout 102. In aspects of the disclosure, the channel lock 104 has a linear portion with bent ends 106 that are secured within openings 108 formed in the bottom wall 58 of the channel member 54. In certain aspects of the disclosure, the bent ends 106 are welded to the bottom wall 58 of the channel member 54 to fixedly secure the channel lock 104 to the proximal end of the channel member 54. In certain aspects of the disclosure, the channel lock 104 has a circular cross-section although other cross-sectional shapes are envisioned.

Figure 5:
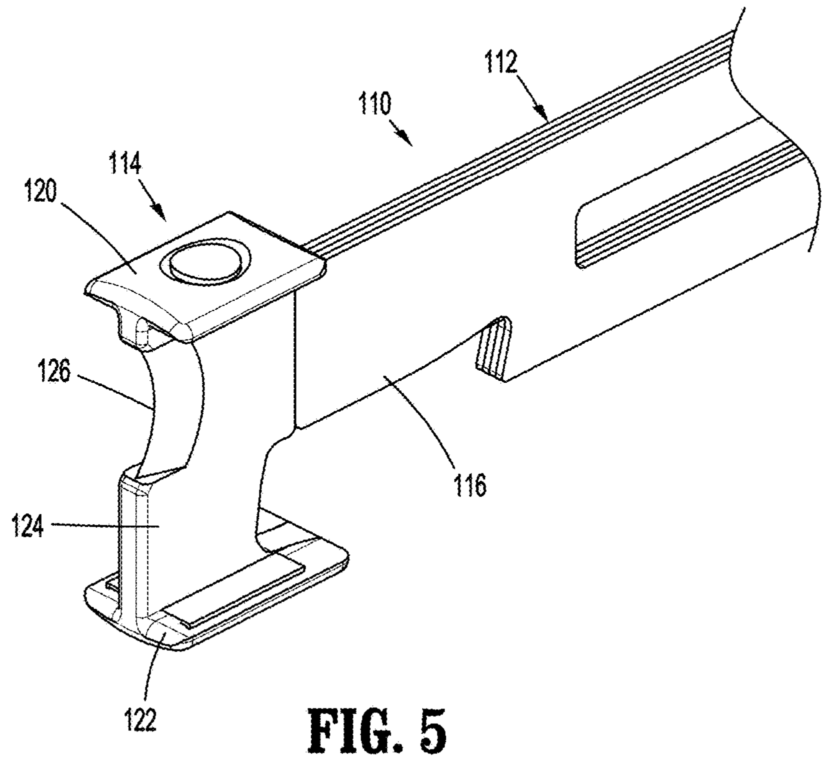
FIG. 5 is a side perspective view of a distal portion of a drive assembly of the stapling device shown in FIG. 1.

FIG. 5 illustrates a drive assembly 110 of the stapling device 10 (FIG. 1) which includes a drive member 112 and a working end 114. In aspects of the disclosure, the drive member 112 includes a proximal portion (not shown) and a distal portion 116. The proximal portion of the drive member 112 is coupled to a drive mechanism (not shown) within the adapter assembly 14 of the stapling device 10 (FIG. 1) such that longitudinal movement of the drive mechanism causes longitudinal movement of the drive assembly 110. The distal portion 116 of the drive member 112 is secured to the working end 114 of the drive assembly 110 such that longitudinal movement of the drive member 112 causes longitudinal movement of the working end 114 in relation to the tool assembly 16 between a drive retracted position and a drive advanced position. In the drive retracted position, the working end 114 of the drive assembly 110 is received in the cutout 102 in the proximal portion of the channel member 54. In aspects of the disclosure, the working end 114 of the drive assembly 110 is welded or pinned to the distal portion 116 of the drive member 112.

The working end 114 of the drive assembly 110 is rigid and has an I-beam configuration with a first beam 120, a second beam 122 and a vertical strut 124. The first beam 120 is secured to, or formed with, one end of the vertical strut 124 and the second beam 122 is secured to, or formed with, an opposite end of the vertical strut 124. In aspects of the disclosure, the vertical strut 124 includes or supports a cutting blade 126. When the drive assembly 110 is in the drive retracted position, the working end 114 of the drive assembly 110 is received within the cutout 102 of the channel member 54 with the vertical strut 124 aligned with the proximal end of the knife slot 62 defined in the channel member 54.

Figure 6:
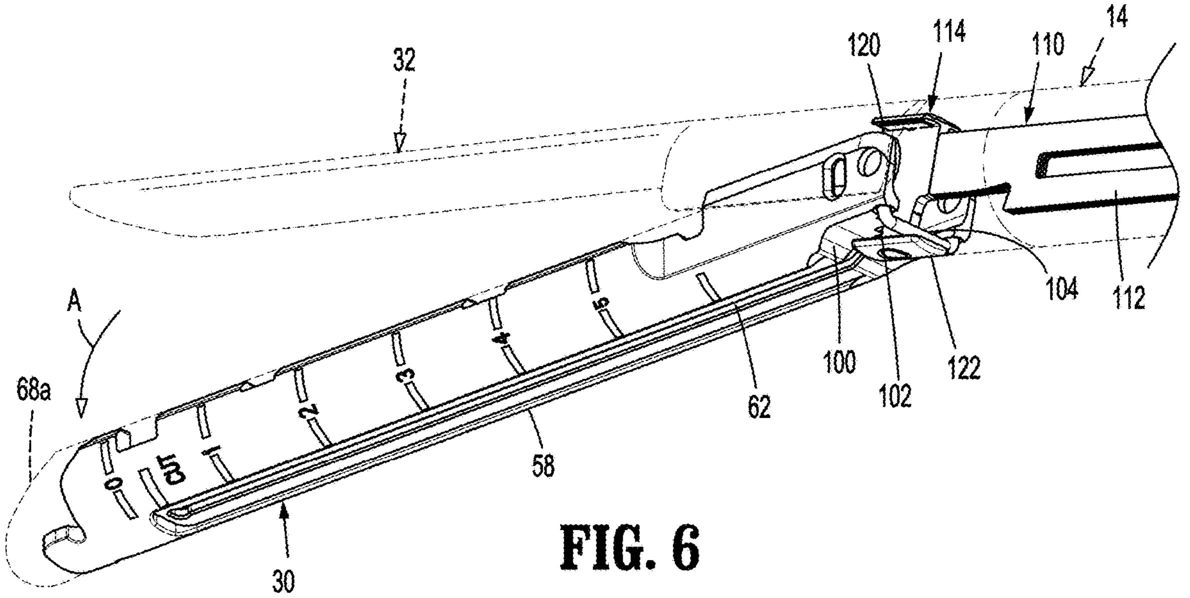
FIG. 6 is a side perspective view of the tool assembly of the stapling device shown in FIG. 1 with a staple cartridge removed from the channel member of the cartridge assembly.

FIG. 6 illustrates the distal portion of the stapling device 10 (FIG. 1) with the drive assembly 110 in the drive retracted position. When the drive assembly 110 is the drive retracted position, the working end 114 of the drive assembly 110 is received in the cutout 102 in the proximal portion of the channel member 54 of the cartridge assembly 30 such that the second beam 122 is positioned proximally of the ramp 100 of the channel member 54 and engaged with the channel lock 104. When the second beam 122 of the working end 114 engages, or is engaged with, the channel lock 104, the working end 114 urges or retains the tool assembly 16 in the open position.

When the stapling device 10 (FIG. 1) is fired, the first beam 120 engages the anvil 32 and the second beam 122 engages the ramp 100 of the channel member 54 such that longitudinal movement of the working end 114 of the drive assembly 110 causes the tool assembly 16 (FIG. 1) to move between the open and clamped positions. The vertical strut 124 of the working end 114 of the drive assembly 110 is positioned proximally of and in alignment with the actuation sled 74 of the staple cartridge 50 such that advancement of the working end 114 of the drive assembly 110 in relation to the anvil 32 and the cartridge assembly 30 causes advancement of the actuation sled 74 within the cartridge body 68 of the staple cartridge 50. As the actuation sled 74 is moved from the sled retracted position towards the sled advanced position, the cam members 82 (FIG. 2A) of the actuation sled 74 move into sequential engagement with the pushers 72 to eject the staples 70 from the cartridge body 68.

Figure 7:
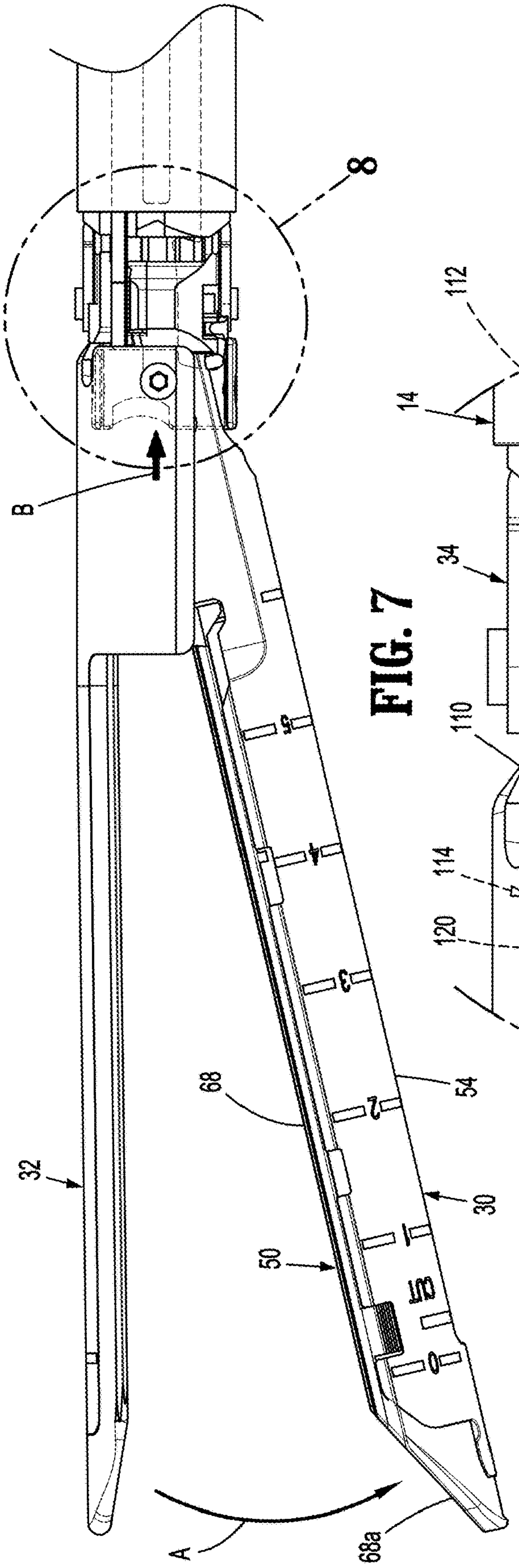
FIG. 7 is a side perspective view of the tool assembly of the stapling device shown in FIG. 1 as the drive assembly is moved from a drive advanced position back to the drive retracted position after the stapling device is fired.
Figure 8:
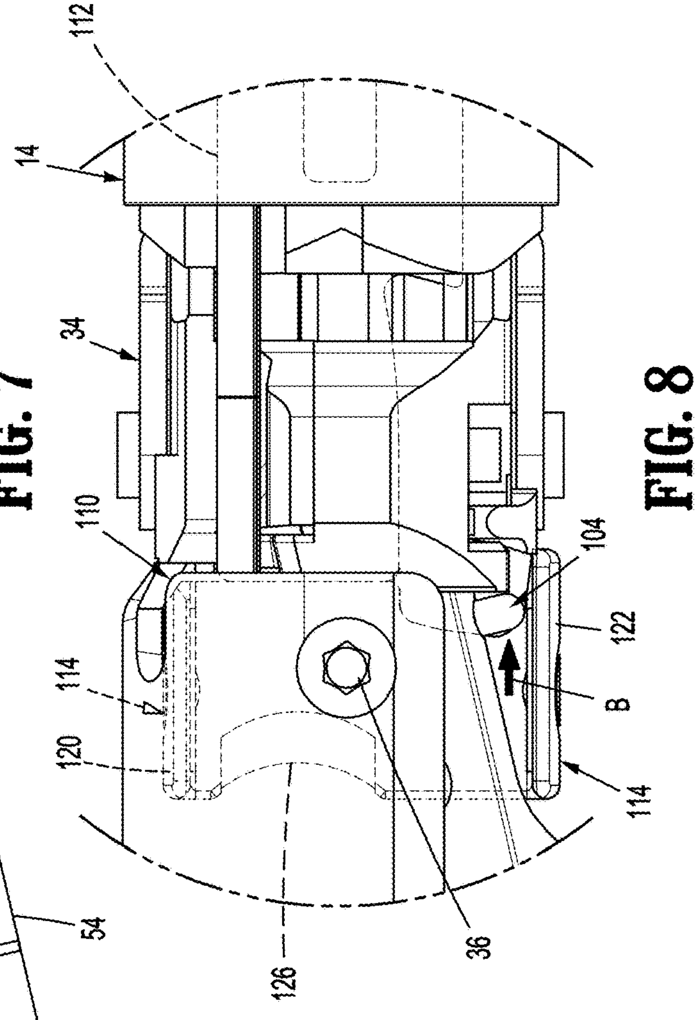
FIG. 8 is an enlarged view of the indicated area of detail shown in FIG. 7.
Figure 9:
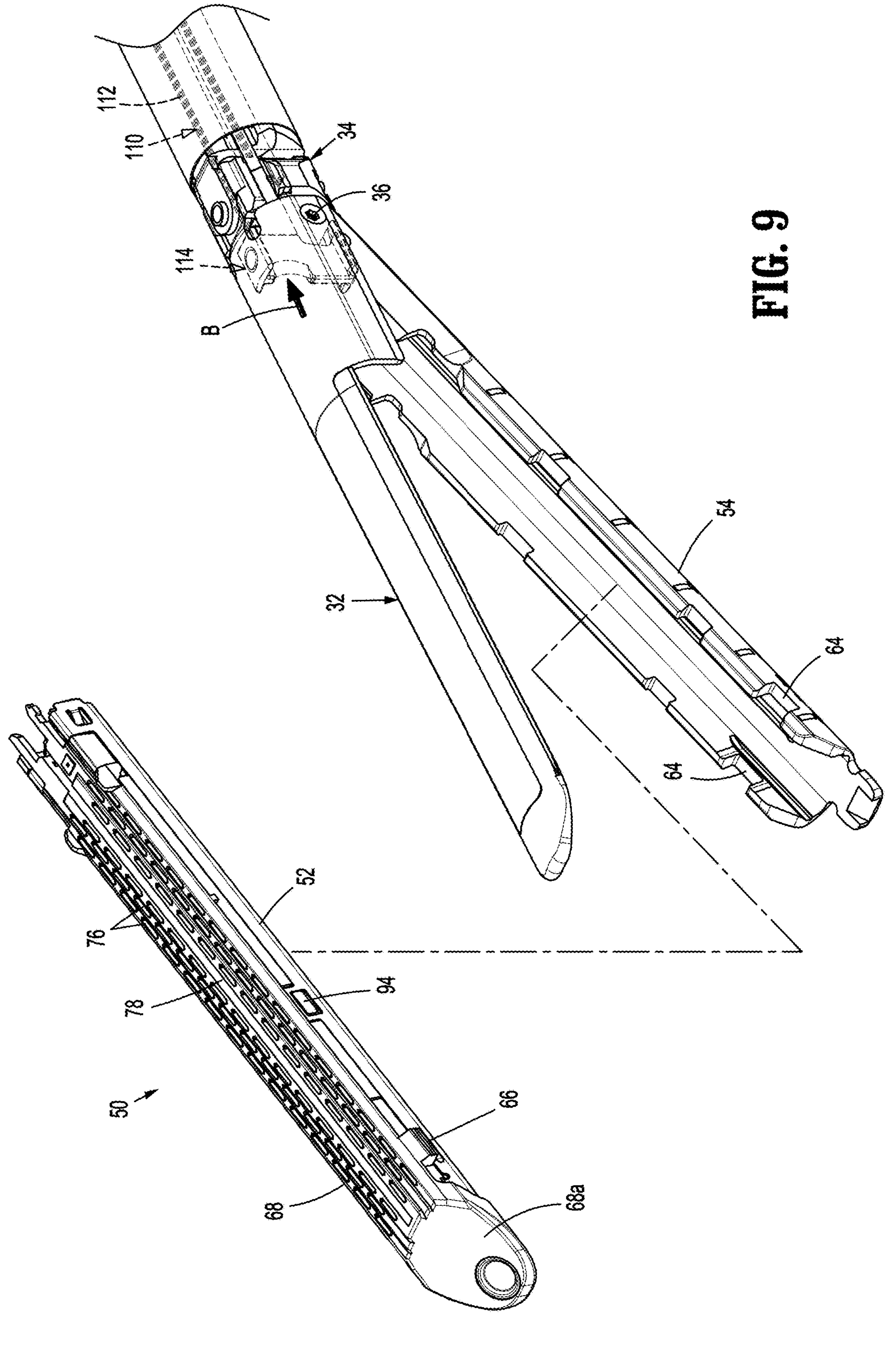
FIG. 9 is a side perspective view of the tool assembly as the staple cartridge is inserted into the channel member of the cartridge assembly of the stapling device shown in FIG. 1.

FIGS. 7-9 illustrate the tool assembly 16 of the stapling device 10 (FIG. 1) as the drive assembly 110 moves in the direction indicated by arrow "B" from the drive advanced position to the drive retracted position. After the stapling device 10 is fired and the drive assembly 110 is returned to the drive retracted position, the second beam 122 engages the channel lock 104 that is secured to the proximal end of the channel member 54 to pivot the channel member 54 and the staple cartridge 50 to the open position. In the open position, the staple cartridge 50 is easily accessible by a clinician to facilitate replacement of the staple cartridge 50 and reuse of the stapling device 10 (FIG. 9).

It is noted that during an endoscopic or laparoscopic surgical procedure, after the tool assembly 16 is inserted through a small diameter cannula (not shown), the tool assembly 16 can be moved to the open position to accommodate tissue prior to clamping the tissue between the anvil 32 and the cartridge assembly 30. When the tool assembly 16 is moved to the open position within a body cavity of a patient, the second beam 122 of the working end 114 of the drive assembly 110 engages the channel lock 104 to retain the cartridge assembly 30 in the open position. The channel lock 104 provides stability to the cartridge assembly 30 to allow the angled distal surface 68*a* of the cartridge body 68 to be used by the clinician to dissect tissue adjacent the surgical site and facilitate proper placement/positioning of the toll assembly about target tissue.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. Also, one skilled in the art will appreciate further features and advantages of the disclosure based on the above-described aspects. Accordingly, the disclosure is not to be limited by what has been particularly shown and described, except as indicated by the appended claims.

What is claimed is:

1. A tool assembly comprising:

an anvil;

a cartridge assembly including a channel member, a staple cartridge, and a channel lock, the channel member being pivotably coupled to the anvil and movable in relation to the anvil between open and clamped positions, the channel member including a proximal portion and having side walls and a bottom wall, the bottom wall defining a first knife slot and extending between the side walls to define a cavity, the staple cartridge receivable within the cavity and including a cartridge body, staples, and an actuation sled, the cartridge body defining a second knife slot and staple receiving slots positioned on opposite sides of the second knife slot, the actuation sled movable within the cartridge body from a sled advanced position to a sled retracted position to eject the staples from the cartridge body, the channel lock secured to the proximal portion of the channel member; and a drive assembly including a drive member and a working end, the drive member movable between a drive retracted position and a drive advanced position to move the actuation sled from the sled retracted position to the sled advanced position, wherein in the drive retracted position, the drive assembly is engaged with the channel lock to retain the channel member of the cartridge assembly in the open position, wherein the channel lock is fixedly secured to the proximal portion of the channel member and remains stationary relative to the channel member during movement of the drive assembly.

2. The tool assembly of claim 1, wherein the channel lock is secured to the bottom wall of the channel member and extends between the side walls of the channel member.

3. The tool assembly of claim 2, wherein the working end of the drive assembly has an I-beam configuration and includes a first beam, a second beam, and a strut interconnecting the first beam and the second beam.

4. The tool assembly of claim 3, wherein the first beam is positioned to engage the anvil and the second beam is positioned to engage the cartridge assembly when the drive assembly is moved from the drive retracted position towards the drive advanced position.

5. The tool assembly of claim 4, wherein the second beam is positioned to engage the channel lock when the drive assembly is in the drive retracted position.

6. The tool assembly of claim 5, wherein the vertical strut includes a cutting blade.

7. The tool assembly of claim 5, wherein the channel lock has a circular cross-section and is secured to the bottom wall of the channel member.

8. The tool assembly of claim 1, wherein the channel lock has a linear portion with bent ends, and the channel member defines openings that receive the bent ends of the channel lock.

9. The tool assembly of claim 1, wherein the bottom wall of the channel member includes a proximal portion defining a cutout that communicates with the first knife slot.

10. The tool assembly of claim 9, wherein the working member of the drive assembly is received within the cutout when the drive assembly is in the drive retracted position.

11. The tool assembly of claim 10, wherein the channel lock is positioned proximally of the working member when the drive assembly is in the drive retracted position.

12. A cartridge assembly comprising:

a channel member including a proximal portion and having side walls and a bottom wall, the bottom wall defining a first knife slot and extending between the side walls to define a cavity;

a staple cartridge receivable within the cavity and including a cartridge body, staples, and an actuation sled, the cartridge body defining a second knife slot and staple receiving slots positioned on opposite sides of the second knife slot, the actuation sled movable within the cartridge body from a sled advanced position to a sled retracted position to eject the staples from the cartridge body; and a channel lock secured to the proximal portion of the channel member and extending between the side walls of the channel member, wherein the channel lock has a circular cross-section and is secured to the bottom wall of the channel member.

13. The cartridge assembly of claim 12, wherein the bottom wall of the channel member includes a proximal portion defining a cutout that communicates with the first knife slot.

14. The cartridge assembly of claim 13, wherein the channel lock extends across the cutout between the side walls of the channel member.

15. The cartridge assembly of claim 12, wherein the channel lock has a linear portion with bent ends, and the channel member defines openings that receive the bent ends of the channel lock.

16. A channel assembly of a cartridge assembly for a surgical stapling device, the channel assembly comprising:

a channel member including a proximal portion and having side walls and a bottom wall, the bottom wall defining a first knife slot and extending between the side walls to define a cavity; and a channel lock secured to the proximal portion of the channel member and extending between the side walls of the channel member, wherein the channel lock has a linear portion with bent ends, and the channel member defines openings that receive the bent ends of the channel lock.

17. The channel assembly of claim 16, wherein the channel lock has a circular cross-section and is secured to the bottom wall of the channel member.

18. The channel assembly of claim 16, wherein the bottom wall of the channel member includes a proximal portion defining a cutout that communicates with the first knife slot.

* * * * *